(12) United States Patent
Izatt et al.

(10) Patent No.: US 8,366,271 B2
(45) Date of Patent: Feb. 5, 2013

(54) SYSTEMS AND METHODS FOR SURGICAL MICROSCOPE AND OPTICAL COHERENCE TOMOGRAPHY (OCT) IMAGING

(75) Inventors: Joseph A. Izatt, Raleigh, NC (US);
Yuankai K. Tao, Cambridge, MA (US);
Cynthia A. Toth, Chapel Hill, NC (US)

(73) Assignee: Duke University, Durham, NC (US)

( * ) Notice: Subject to any disclaimer, the term of this patent is extended or adjusted under 35 U.S.C. 154(b) by 82 days.

(21) Appl. No.: 13/010,497

(22) Filed: Jan. 20, 2011

(65) Prior Publication Data

US 2012/0092615 A1    Apr. 19, 2012

Related U.S. Application Data

(60) Provisional application No. 61/296,689, filed on Jan. 20, 2010.

(51) Int. Cl.
A61B 3/14    (2006.01)
A61B 3/00    (2006.01)
(52) U.S. Cl. ......... 351/206; 351/219; 351/246; 351/247
(58) Field of Classification Search .................. 351/205, 351/206, 219, 246, 247; 356/479
See application file for complete search history.

(56) References Cited

U.S. PATENT DOCUMENTS

| | | |
|---|---|---|
| 5,493,109 A | 2/1996 | Wei et al. |
| 5,963,301 A | 10/1999 | Volk |
| 7,791,794 B2 | 9/2010 | Reimer et al. |
| 7,839,494 B2 | 11/2010 | Reimer et al. |
| 2012/0184846 A1 | 7/2012 | Izatt et al. |

FOREIGN PATENT DOCUMENTS

WO    WO2012/100030 A2    7/2012

OTHER PUBLICATIONS

SDI®/BIOM® "Still the Standard in Wide-Angle Viewing for All Microscope Models!", Distributed by Insight Instruments, Inc.

*Primary Examiner* — Jack Dinh
(74) *Attorney, Agent, or Firm* — Olive Law Group, PLLC

(57) ABSTRACT

A surgical microscope assembly includes a microscope main objective and microscope imaging optics. The microscope main objective and microscope imaging optics define a viewing beam path that passes from a sample through the microscope main objective and the microscope imaging optics. The assembly includes an optical coherence tomography (OCT) unit having an illumination beam and a collection beam and a beamsplitter between the microscope main objective and the microscope imaging optics. The beamsplitter is configured to direct a portion of light from the microscope main objective to the microscope imaging optics and to direct another portion of light from the microscope main objective to the OCT unit collection beam. The beamsplitter is further configured to direct an illumination beam from the OCT unit to the microscope main objective and to the sample. A beam forming unit is between the OCT unit and the beamsplitter. The beam forming unit is configured to form the illumination beam of the OCT unit so as to generally correspond to a size of the microscope main objective.

25 Claims, 27 Drawing Sheets

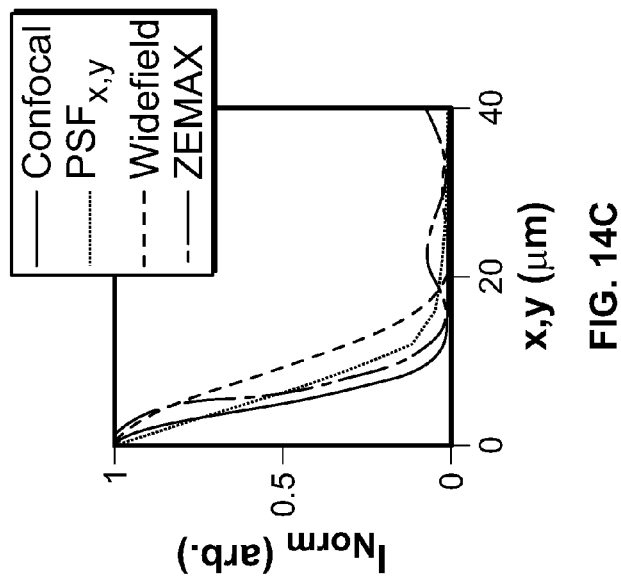
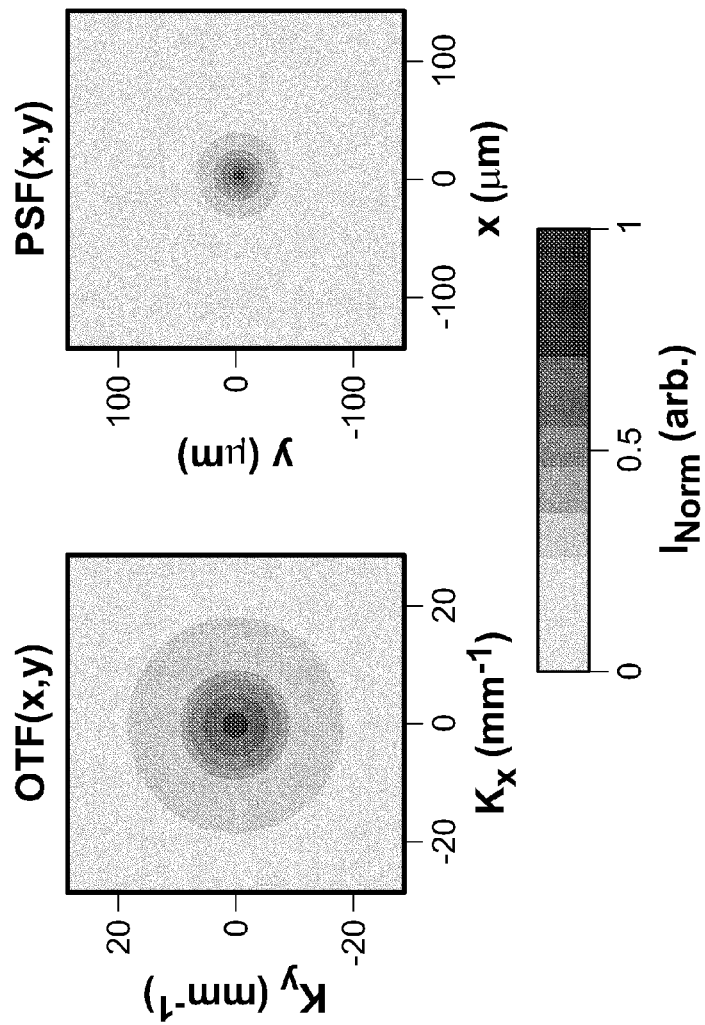
FIG. 14A
FIG. 14B
FIG. 14C

SYSTEMS AND METHODS FOR SURGICAL MICROSCOPE AND OPTICAL COHERENCE TOMOGRAPHY (OCT) IMAGING

RELATED APPLICATION

The present invention claims priority to U.S. Application Ser. No. 61/296,689, filed Jan. 20, 2010, the disclosure of which is hereby incorporated by reference in its entirety.

STATEMENT OF GOVERNMENT SUPPORT

The present invention was produced in part using funds from the Federal Government under NIH/NEI grant No. R21 EY019411-A1 entitled "Real Time Intraoperative SDOCT for Vitreoretinal Surgery." The Federal government has certain rights in this invention.

FIELD

The current invention relates to ophthalmic surgical microscopes, and in particular, to ophthalmic surgical microscopes using optical coherence tomography.

BACKGROUND

Since its introduction in the early 1990's, optical coherence tomography (OCT) has emerged as a promising imaging modality for micrometer-scale noninvasive imaging in biological and biomedical applications. Its relatively low cost and real-time, in vivo capabilities have fueled the investigation of this technique for applications in retinal and anterior segment imaging in ophthalmology (e.g., to detect retinal pathologies), early cancer detection and staging in the skin, gastrointestinal, and genitourinary tracts, as well as for ultrahigh resolution imaging of entire animals in embryology and developmental biology.

Conventional OCT systems are essentially range-gated low-coherence interferometers that have been configured for characterization of the scattering properties of biological and other samples. By measuring singly backscattered light as a function of depth, OCT fills a valuable niche in imaging of tissue ultrastructure, and provides subsurface imaging with high spatial resolution (~1-10 µm) in three dimensions and high sensitivity (>110 dB) in vivo with no contact needed between the probe and the tissue. OCT is based on the one-dimensional technique of optical coherence domain reflectometry (OCDR), also called optical low-coherence reflectometry (OLCR). See Youngquist, R. C., S. Carr, and D. E. N. Davies, *Optical Coherence Domain Reflectometry: A New Optical Evaluation Technique.* Opt. Lett., 1987. 12: p. 158; Takada, K., et al., *New measurement system for fault location in optical waveguide devices based on an interferometric technique.* Applied Optics, 1987. 26(9): p. 1603-1606; and Danielson, B. L. and C. D. Whittenberg, *Guided-wave Reflectometry with Micrometer Resolution.* Applied Optics, 1987. 26(14): p. 2836-2842. In some instances of time-domain OCT, depth in the sample is gated by low coherence interferometry. The sample is placed in the sample arm of a Michelson interferometer, and a scanning optical delay line is located in the reference arm.

The time-domain approach used in conventional OCT has been used in supporting biological and medical applications. An alternate approach involves acquiring as a function of optical wavenumber the interferometric signal generated by mixing sample light with reference light at a fixed group delay. Two methods have been developed which employ this Fourier domain (FD) approach. The first is generally referred to as Spectral-domain OCT (SDOCT). SDOCT uses a broadband light source and achieves spectral discrimination with a dispersive spectrometer in the detector arm. The second is generally referred to as swept-source OCT (SSOCT). SSOCT time-encodes wavenumber by rapidly tuning a narrowband source through a broad optical bandwidth. Both of these techniques can provide improvements in SNR of up to 15-20 dB when compared to time-domain OCT, because SDOCT and SSOCT capture the complex reflectivity profile (the magnitude of which is generally referred to as the "A-scan" data or depth-resolved sample reflectivity profile) in parallel. This is in contrast to time-domain OCT, where destructive interference is employed to isolate the interferometric signal from only one depth at a time as the reference delay is scanned.

Surgical visualization has changed drastically since its inception, incorporating larger, more advanced optics toward increasing illumination and field-of-view (FOV). However, the limiting factor in vitreoretinal surgery remains the ability to distinguish between tissues with subtle contrast, and to judge the location of an object relative to other retinal substructures. S. R. Virata, J. A. Kylstra, and H. T. Singh, Retina 19, 287-290 (1999); E. Garcia-Valenzuela, A. Abdelsalam, D. Eliott, M. Pons, R. Iezzi, J. E. Puklin, M. L. McDermott, and G. W. Abrams, Am J Ophthalmol 136, 1062-1066 (2003). Furthermore, increased illumination to supplement poor visualization is also limited by the risks of photochemical toxicity at the retina. S. Charles, Retina 28, 1-4 (2008); J. R. Sparrow, J. Zhou, S. Ben-Shabat, H. Vollmer, Y. Itagaki, and K. Nakanishi, Invest Ophthalmol Vis Sci 43, 1222-1227 (2002). Finally, inherent issues in visualizing thin translucent tissues, in contrast to underlying semitransparent ones, require the use of stains such as indocyanine green, which is toxic to the retinal pigment epithelium. F. Ando, K. Sasano, N. Ohba, H. Hirose, and O. Yasui, Am J Ophthalmol 137, 609-614 (2004); A. K. Kwok, T. Y. Lai, K. S. Yuen, B. S. Tam, and V. W. Wong, Clinical & experimental ophthalmology 31, 470-475 (2003); J. Lochhead, E. Jones, D. Chui, S. Lake, N. Karia, C. K. Patel, and P. Rosen, Eye (London, England) 18, 804-808 (2004).

Spectral domain optical coherence tomography (SDOCT) has demonstrated strong clinical success in retinal imaging, enabling high-resolution, motion-artifact-free cross-sectional imaging and rapid accumulation of volumetric macular datasets. N. A. Nassif, B. Cense, B. H. Park, M. C. Pierce, S. H. Yun, B. E. Bouma, G. J. Tearney, T. C. Chen, and J. F. de Boer, Optics Express 12, 10 (2004); M. Wojtkowski, V. J. Srinivasan, T. H. Ko, J. G. Fujimoto, A. Kowalczyk, and J. S. Duker, Optics Express 12, 2404-2422 (2004). Current generation SDOCT systems achieve <5 µm axial resolutions in tissue, and have been used to obtain high resolution datasets from patients with neovascular AMD, high risk drusen, and geographic atrophy. M. Stopa, B. A. Bower, E. Davies, J. A. Izatt, and C. A. Toth, Retina 28, 298-308 (2008). Other implementations of optical coherence tomography (OCT) including swept-source optical coherence tomography (SSOCT) may offer similar performance advantages.

Preoperative diagnostic imaging using current generation SDOCT systems have demonstrated the ability to provide volumetric datasets of pathologic areas that are otherwise barely visible.

SUMMARY OF EMBODIMENTS OF THE INVENTION

A surgical microscope assembly including microscope imaging optics having a microscope main objective. The microscope imaging optics define one or more viewing beam paths that pass from a sample through the microscope main objective and the microscope imaging optics. The assembly includes an optical coherence tomography (OCT) unit having an illumination beam and a collection beam and a beamsplitter positioned in the one or more microscope viewing beam paths. The beamsplitter is configured to direct a portion of light from the sample to the microscope imaging optics and to direct another portion of light from the sample to the OCT unit collection beam. The beamsplitter is further configured to direct an illumination beam from the OCT unit to the sample. A beam forming unit is between the OCT unit and the beamsplitter. The beam forming unit is configured to form the illumination beam of the OCT unit so as to substantially correspond to a size of the microscope main objective.

In some embodiments the surgical microscope assembly includes a vitreoretinal viewing optics unit configured to transmit light received from the sample to the microscope main objective for vitreoretinal imaging by the microscope imaging optics and to receive the illumination beam of the OCT unit from the microscope main objective. In some embodiments, the vitreoretinal viewing optics unit includes a contact lens element for contacting a sample. In some embodiments, the vitreoretinal viewing optics unit comprises a non-contact lens configured for positioning adjacent the sample and a reduction lens configured for positioning adjacent the microscope main objective.

In some embodiments, the beam splitter includes a dichroic mirror. In some embodiments, the beam forming unit is configured to form the illumination beam of the OCT unit so as to substantially correspond to a size of a binocular viewing path area of the microscope main objective.

In some embodiments, the beam forming unit is configured to magnify the illumination beam of the OCT unit. The sample may include an ocular sample, such as an ocular fundus.

In some embodiments, the beam forming optical assembly comprises an adjustable Keplerian telescope. In some embodiments, the beam forming optical assembly includes at least two lenses being configured to adjustably focus and/or magnify the illumination beam of the OCT unit. In some embodiments, the microscope imaging optics includes microscope magnification optics, and the beamsplitter is positioned between the microscope main objective and the microscope magnification optics. In some embodiments, the beam forming unit is configured to form the illumination beam of the OCT unit so as to reduce image vignetting.

According to some embodiments of the present invention, a surgical microscope assembly includes microscope imaging optics having a microscope main objective. The microscope imaging optics define a viewing beam path that passes from a sample through the microscope main objective and the microscope imaging optics. The assembly includes an optical coherence tomography (OCT) unit having an illumination beam and a collection beam. A beamsplitter is configured to direct a portion of light from the sample to the to the microscope main objective and to direct another portion of light from the sample to the OCT unit. The beamsplitter is further configured to direct light from the illumination beam of the OCT unit to the sample. A beam forming unit is between the OCT unit and the beamsplitter and is configured to form the illumination beam of the OCT unit to substantially correspond to a beam path of the microscope main objective.

In some embodiments, a vitreoretinal viewing optics unit is configured to transmit light received from the sample to the microscope main objective for vitreoretinal imaging by the microscope imaging optics. In some embodiments, the vitreoretinal viewing optics unit comprising a non-contact lens configured for positioning adjacent the sample and a reduction lens configured for positioning adjacent the microscope main objective, and the non-contact lens and the reduction lens are configured to provide a vitreoretinal view of an ocular sample. In some embodiments, the beamsplitter is positioned between the non-contact lens and the reduction lens.

According to some embodiments of the present invention, methods of imaging a sample with an optical coherence tomography (OCT) unit having an illumination beam and a collection beam and a microscope having microscope imaging optics with a microscope main objective are provided. A portion of light from the microscope main objective is directed to additional portions of the microscope imaging optics. Another portion of light is directed from the microscope main objective to the OCT unit collection beam. The illumination beam of the OCT unit is formed to substantially correspond to a beam path of the microscope main objective. The formed illumination beam is directed from the OCT unit to the microscope main objective and to the sample.

According to some embodiments of the present invention, methods of imaging a sample with an optical coherence tomography (OCT) unit having an illumination beam and a collection beam and a microscope having microscope imaging optics with a microscope main objective are provided. A portion of light is directed from the sample to the to the microscope main objective. Another portion of light is directed from the sample to the OCT unit collection beam. The illumination beam of the OCT unit is formed to substantially correspond to a beam path of the microscope main objective, and the formed light is directed from the illumination beam of the OCT unit to the sample.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 14A is a graph of the focal plane cross-section of a lateral optical transfer function (OTF) measuring a resolution of a microscope mounted OCT unit according to some embodiments of the present invention.

FIG. 14B is a graph of the point spread function (PSF) of the focal plane calculated from the OTF of FIG. 14A.

FIG. 14C is a graph of the PSF cross-section compared with theoretical values for confocal and wide-field imaging systems and Zemax simulations.

FIG. 15A illustrates a volumetric rendering, and FIG. 15B illustrates a summed-voxel-projection, which show both the instrument and a piece of glial tissue extruding from the optic nerve. The illumination power is 700 µW, and the scale bar is three degrees.

FIG. 20C is a video of a volumetric rendering of an 8×8 volumetric dataset of human macula. B-scans were acquired with 1024×1024 pixels (lateral×spectral) at a line-rate of 20 kHz, and volumes were acquired with 200 B-scans at an illumination power 700 µW. The scale bar is 2 degrees.

DETAILED DESCRIPTION OF EMBODIMENTS

Figure 1A:
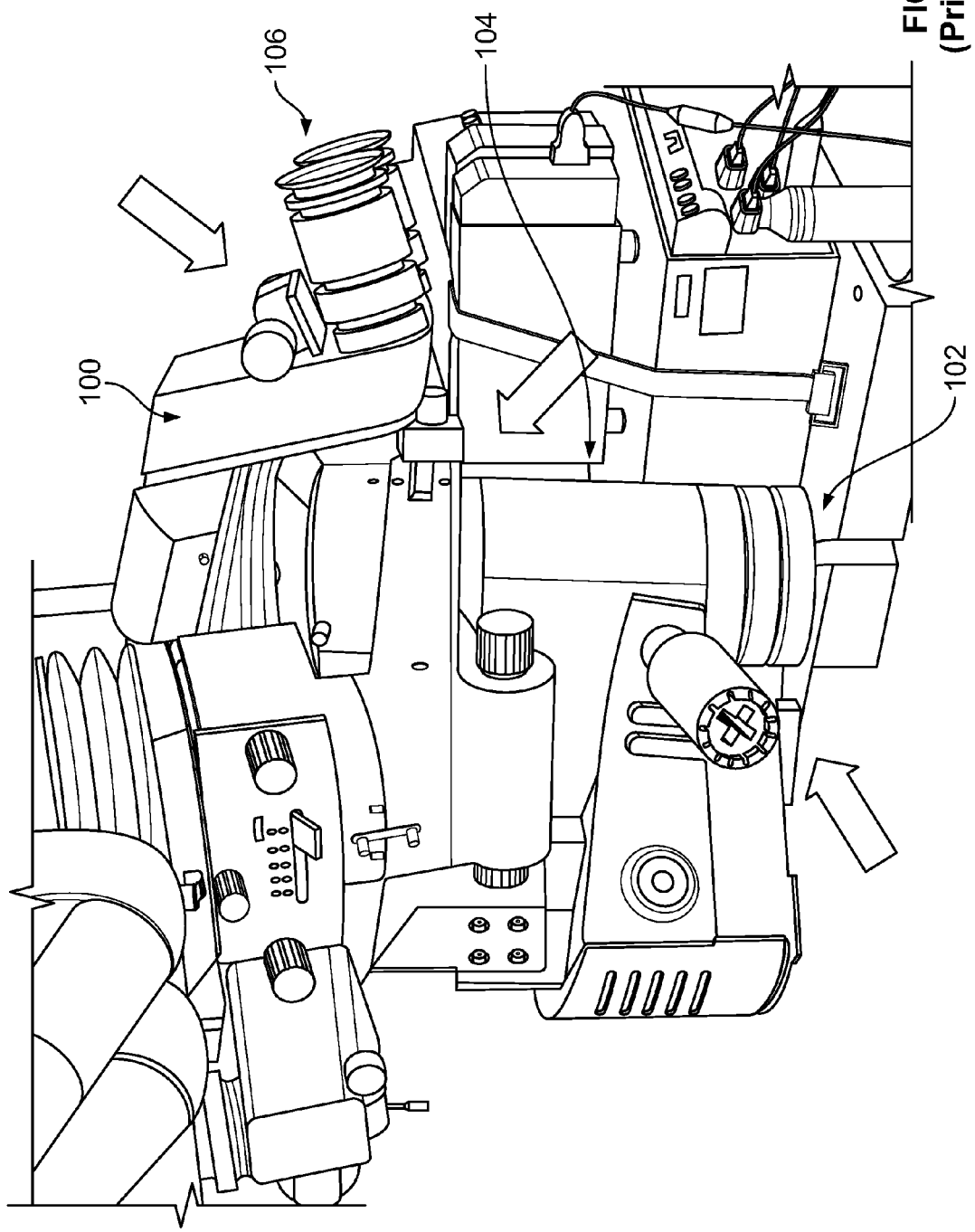
FIG. 1A is a perspective view of a conventional surgical microscope.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

In some embodiments, OCT imaging of a surgical specimen or operating field in conjunction with standard surgical microscopy may be used to give the surgeon an additional, two- or three-dimensional view of structures which may be difficult or impossible for the surgeon to visualize with a standard microscope alone. These structures may be difficult to visualize because they are beyond the resolution limit of the microscope optics or of the surgeon's eye, or are poorly lit, translucent, opaque, or buried in a translucent or opaque structure. OCT 2D images may be acquired in a cross-sectional view which complements the en-face view which the surgeon sees through the surgical microscope. OCT 3D volume images convey more information regarding the structures and their spatial orientation and relationships than is available in the surgeon's standard view through the microscope.

Figure 1B:
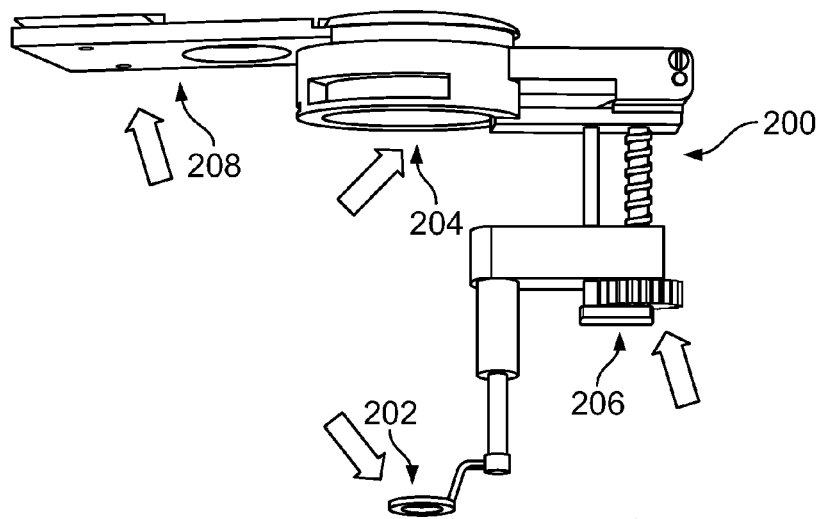
FIG. 1B is a perspective view of conventional vitreoretinal viewing lenses.
Figure 1C:
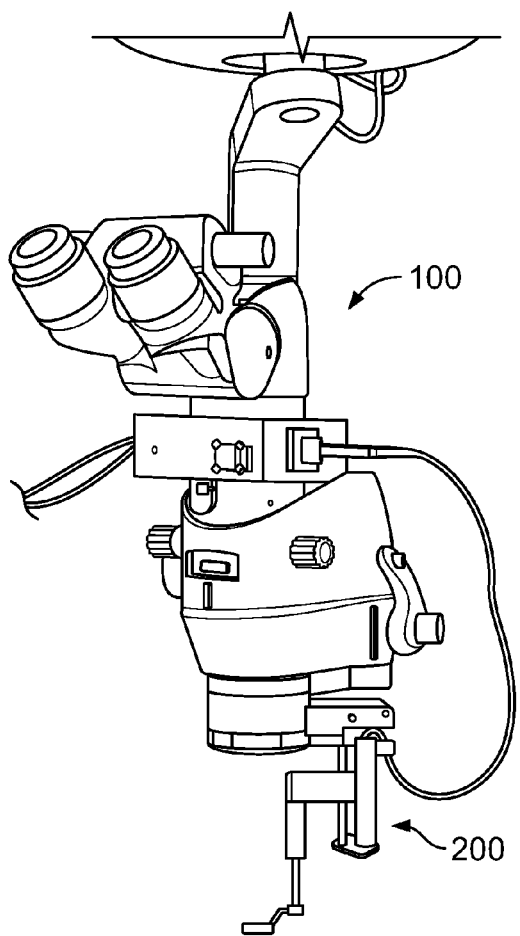
FIG. 1C is a perspective view of a conventional surgical microscope with a vitreoretinal viewing lens attachment.

As illustrated in FIG. 1A, a surgical microscope 100 includes an objective lens 102, a microscope imaging optics unit 104 and an eyepiece 106. As illustrated in FIG. 1B, a vitreoretinal viewing optics unit 200 includes a non-contact lens 202 configured for positioning adjacent the subject's eye and a reduction lens 204 that is configured for positioning adjacent a microscope main objective lens. The vitreoretinal viewing optics unit 200 further includes an adjustable arm 206 for adjusting the distance between the non-contact lens 202 and the reduction lens 204, and a hinged attachment arm 208. As illustrated in FIG. 1C, the vitreoretinal viewing optics unit 200 is attached to the surgical microscope 100. In some cases, the vitreoretinal viewing optics unit 200 may be configured so that the unit 200 is movable between the position illustrated in FIG. 1C and a retracted position in which the vitreoretinal viewing optics unit 200 is rotated out of the optical path of the microscope 100. The surgical microscope 100 illustrated in FIG. 1A is a Leica microscope (Leica Microsystems, Wetzlar, Germany); however, any suitable surgical microscope may be used. The vitreoretinal viewing optics unit 200 in FIG. 1B is an Oculus Binocular Indirect Ophthalmo Microscope (BIOM3) adapter (Insight Instruments, Inc., Stuart, Fla., U.S.A.); however, any suitable vitreoretinal viewing adapter for visualizing the ocular fundus may be used, including a single reduction lens for visualizing the ocular fundus, such as contact lenses available from Volk Optical, Mentor, Ohio, U.S.A.

With respect to ocular surgery, OCT imaging of a patient's eye in conjunction with standard ocular/video fundus viewing during ocular surgery of the anterior or posterior segment of the eye may be performed. The standard microscope setup most often used for ocular surgery includes a high-quality stereo zoom microscope with a shared main objective design which is suspended above the subject's eye and is illustrated in FIGS. 1A and 1D. As illustrated in FIG. 1D, stereo zoom microscope includes an objective lens 102, and the microscope optics 104 include two or more parallel optical imaging channels 112, 114 above the shared objective 102 (assuming the microscope is oriented in the normal vertical orientation). Each of the parallel optical imaging channels 112, 114 include some combination of zoom optics, beam splitters for further splitting the optical beam path (to allow for assistant viewports, video recording of surgery, white light illumination, laser surgery, etc.), and ocular eyepieces 106 for the surgeon. In the space between the optical imaging channels 112, 114 and the shared objective 102, the ray bundles carrying the optical image of the patient's eye to the surgeon's eyepieces 106 are essentially parallel, and this space is referred to herein as the "infinity space" of the microscope. It should be understood that the infinity space may be generally parallel; however, deviations and imperfections within the infinity space may occur. The shared main objective 102 collimates image-bearing light coming from the object plane of the microscope into this infinity space, whereupon sub-apertures of this light are divided among the parallel optical imaging channels 112, 114. Standard microscopes used for ocular surgery have a working distance (WD) which is approximately equal to the focal length of the main objective, typically around 10-20 cm.

Notable features for surgical (or any other) microscopes, as well as for OCT systems, include field of view (FOV), resolution (R), angular light collection efficiency, and lack of image vignetting. FOV is defined as the lateral range over which the microscope forms an image of the object which is conveyed to the image plane, i.e. the surgeon's own retinas or a video camera. Resolution is defined as the length of the minimum observable feature of the object which is observable in the image plane. Resolution depends upon the wavelength (lambda) of the illumination light and the numerical aperture (NA) of the imaging lens or lens system. A standard formula for resolution is given by Abbe's formula according to:

$$R = \text{lambda}/(2*NA). \quad \text{Eq. (1)}$$

NA is a dimensionless number which characterizes the range of angles over which an optical system can accept light, defined by:

$$NA = n \sin(\theta/2) \quad \text{Eq. (2)}$$

Here, n is the index of refraction of the medium and $\theta$ is the acceptance cone angle of light collected by the lens. Note that since resolution depends upon the range of angles over which light is accepted, optical systems with higher resolution also have higher angular light collection efficiency. In OCT systems, higher light collection efficiency translates directly to brighter OCT images. Vignetting can be a problem in poorly designed optical systems in which portions of the optical image may be physically blocked by the edges of inappropriately positioned apertures in the optical system. OCT systems can be particularly prone to vignetting because 2 and 3 dimensional OCT images are formed by physically scanning the OCT sample arm beam in one or two lateral dimensions across the sample under interrogation. If it is desirable to utilize the full aperture of one or more of the optical elements of the OCT system to maximize NA, for example, in order to maximize OCT image resolution and brightness, then it is critical that the sample arm beam be arranged to pivot through those elements rather than to scan across them. This is exactly the case for OCT imaging of the retina, in which the patient's own cornea and crystalline lens operate as a compound lens used to focus the OCT sample arm beam onto the retina. However, the area over which these physiological optics are near diffraction limited is typically only the central 2 or 3 mm of their diameter, and the entire available aperture of the eye is physically limited by the anatomical iris to a maximum aperture of about 7 mm diameter. It is acceptable for first-order optical calculations to treat the compound physiological lens as a single ideal lens placed at the position of the patient's iris plane, with a focal length of about 24 mm. Thus, for OCT systems designed for scanning the retina with optimal resolution, it is desirable that the sample arm beam size be about 2-3 mm diameter at the iris plane position, and be designed to pivot through the ophthalmic lens rather than scan across it.

The zoom optics of stereo zoom microscopes used for ocular surgery typically allow for the field-of-view and resolution of the microscope to be continuously varied over some pre-set range, while keeping the working distance essentially constant. However, whatever the zoom setting, the resolution and angular collection efficiency obtainable in each of the parallel optical imaging channels is always less than the resolution and angular collection efficiency which could be obtained using the full optical aperture of the main objective. This is because in order to have multiple parallel optical imaging channels (allowing for stereo viewing and separate optical paths for accessories), each of those imaging channels use only a sub-aperture of the entire aperture of the main objective. The numerical aperture of each of the sub-apertures is typically substantially less than the numerical aperture of the main objective, often by a factor of 3-5×. The prior art implementations of combining OCT systems with surgical microscopes all use narrow OCT beams which occupy only a sub-aperture of the main objective, either by introducing the OCT beam into an existing parallel optical path above the shared objective (U.S. Pat. Nos. 7,791,794 and 7,839,494) or by introducing a narrow OCT beam using a beamsplitter into the infinity space above the main objective (U.S. Pat. No. 5,493,109). Thus, these prior art systems provide for less than optimal OCT resolution and angular light collection efficiency because their OCT beams only occupy a fraction of the optical aperture of the main objective, and thus collect light from the sample with a lower range of angles than the main objective allows for. Also, prior art implementations of OCT surgical microscopes do not provide means for pivoting the sample arm beam through the physiological lens in order to avoid OCT retinal image vignetting simultaneous with maximizing resolution and light collection efficiency. The object of this invention is to provide for a means of combining the sample aim of an OCT system with surgical microscope optics in such a way as to allow for the resolution and brightness of the OCT images obtained to be as high as possible, while still preserving the same field-of-view and zooming capability as the microscope optics and avoiding OCT image vignetting.

As shown in FIG. 1D, a conventional stereo zoom microscope 100 as is commonly used for intrasurgical applications including anterior segment ocular surgery includes one or more parallel optical imaging channels 112, 114 which may contain zoom optics and eyepieces 106. The optical imaging channels 112, 114 share a common main objective 102 which may be a highly optimized achromatic lens, but is here approximated as being a simple ideal lens having a focal length $f_4$. The working distance (denoted WD) to the object plane of the microscope is also $f_4$, thus above the main objective all of the light rays collected from the object are essentially parallel. The field of view of the microscope is denoted FOV and is controllable by the surgeon using the zoom optic controls of the microscope. The microscope may provide for white light illumination of the object either through an illumination source 110 internal to the microscope 100 and above the shared objective 102, as depicted, or elsewhere. The resolution and angular light collection efficiency available through any of the optical imaging channels of the microscope are functions of the NA of the imaging channels according to Eq. 1, where the NA of an imaging channel depends upon the collection acceptance angle of the channel.

For example, in FIG. 1D. The collection angle of the imaging channel depicted is $\theta_3$. This collection angle is less than the collection angle of the entire shared objective (which is $\theta_2$) according to the ratio of the diameters of the individual imaging channel and the share objective, approximately according to:

$$\frac{\theta_3}{\theta_2} = \frac{a_4}{a_3} \qquad \text{Eq. (3)}$$

Figure 1E:
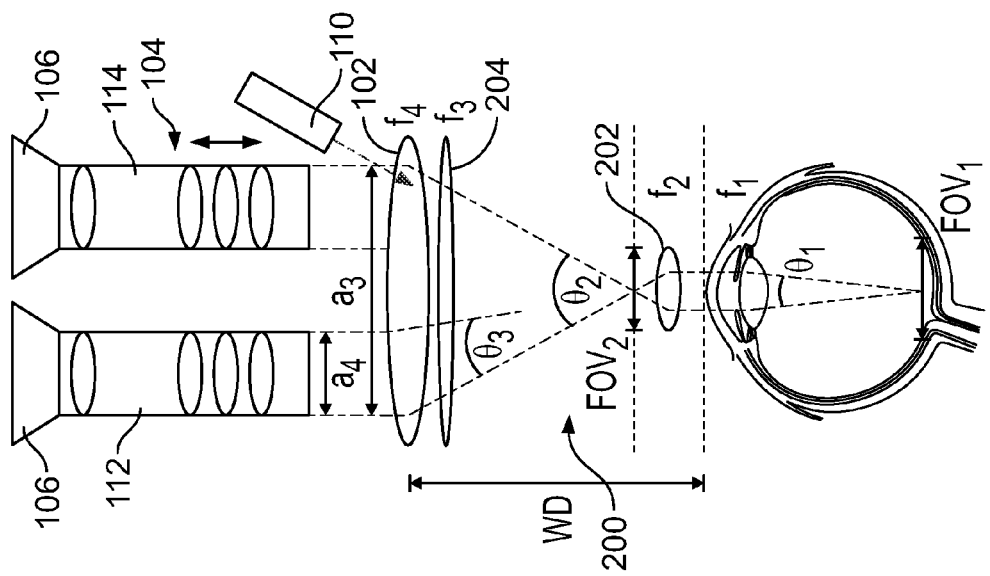
FIG. 1E is a schematic diagram of a conventional surgical microscope with a vitreoretinal viewing lens attachment.
Figure 1D:
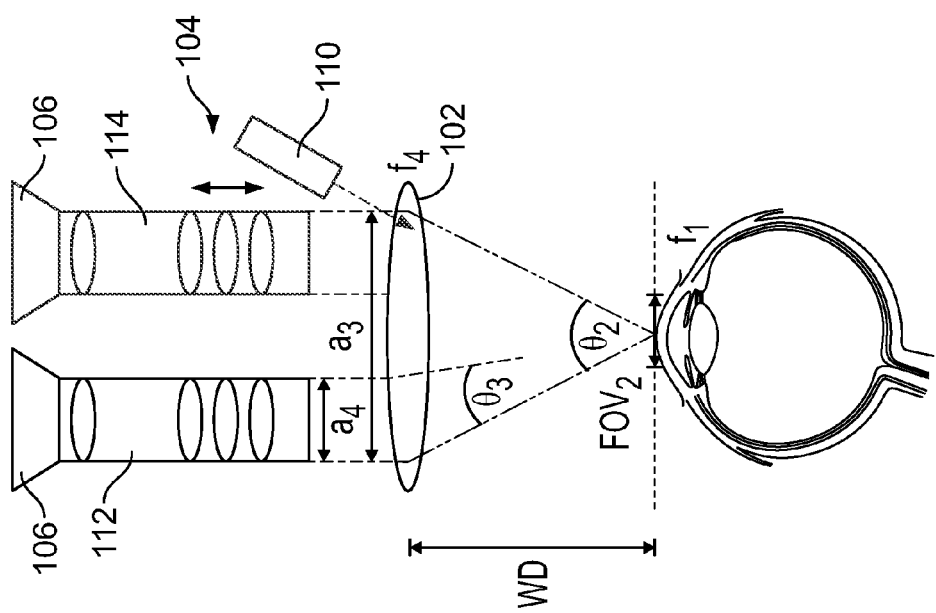
FIG. 1D is a schematic diagram of a conventional surgical microscope.

FIG. 1E depicts a conventional stereo zoom microscope as in FIG. 1D which is converted to image a patient's retina by a vitretinal viewing optics unit 200 including two extra lenses 202, 204 in combination with the patient's own ophthalmic lens. The compound ophthalmic lens consisting of the cornea and crystalline lens is here approximated by a single lens with focal length $f_1$, which is positioned at the iris plane of the patient's eye. A retinal magnifying lens 202 with focal length $f_2$ is placed in close proximity to the patient's cornea, typically 5-10 mm away. These two lenses act together to bring a real image of the patient's retina to an intermediate image plane, located approximately a distance $f_2$ above the retinal magnifying lens if the patient is focused at infinity. This intermediate image plane then serves as the object plane for the surgical microscope, which acts to re-form an image of this plane at the image plane of the microscope, for example on the surgeon's own retina or on a video camera positioned in one of the parallel optical imaging channels above the shared objective. For the convenience of the surgeon, an additional reducing lens 204 with focal length $f_3$ is often mounted together with the retinal magnifying lens on a common assembly which can be pivoted into position below the shared objective lens when needed during surgery. When this assembly is not in place, the surgical microscope will function optically as depicted in FIG. 1D, with the anterior segment of the patient's eye in focus so that the surgeon can perform surgical procedures there. When the surgeon needs to bring the patient's retina into view, the assembly can be rotated into the position depicted in FIG. 1E. The purpose of the reducing lens within the optical assembly is to add slightly more power to the shared objective when the retinal assembly is in place so that the object plane of the microscope is raised to correspond to the intermediate image plane position in FIG. 1E. If the reducing lens were not present, then the surgeon would have to physically raise or lower the whole microscope when switching back and forth from anterior to posterior segment viewing.

The retinal magnifying lens typically has a focal length which is shorter than the focal length of the patient's own eye, so these two lenses in combination act as a telescope to deliver a de-magnified image of the patient's retina to the intermediate image plane. Thus the field of view at the intermediate image plane is smaller than that at the retina according to:

$$\frac{FOV_2}{FOV_1} = \frac{f_2}{f_1} \qquad \text{Eq. (4)}$$

The telescope also acts to magnify the collection angle of image light emanating from the retina, according to:

$$\frac{\theta_2}{\theta_1} = \frac{f_1}{f_2} \qquad \text{Eq. (5)}$$

The retinal magnifying lens and reducing lens combination are optimally designed so that the cone angle of image light emitted by the retinal magnifying lens is matched to the cone acceptance angle of the main objective lens of the microscope. Thus, for the retinal imaging configuration depicted in FIG. 1E, the collection angle of image light for any optical imaging channel of the surgical microscope is given by combining Eqs. (3) and (5), resulting in:

$$\frac{\theta_3}{\theta_1} = \frac{a_4}{a_3} \qquad \text{Eq. (6)}$$

Thus, the resolution and brightness of retinal images observed in any imaging channel of the retinal microscope depicted in FIG. 1E is reduced compared to the resolution and brightness captured by the shared objective by the same ratio as in Eq. (6).

It should be noted that an alternate approach to that depicted in FIG. 1E for intrasurgical imaging of the retina is simply to place an essentially flat-topped contact lens in contact with the patient's eye. This contact lens essentially negates the optical power of the patient's cornea, which is where the bulk of physiological refraction occurs. With this contact lens in place, the standard surgical microscope depicted in FIG. 1D can then be lowered down until its object plane coincides with the retina of the patient. Unlike the approach of FIG. 1E which is suitable for wide-field viewing, this approach is only suitable for narrow-field imaging of the patient's retina, since substantial vignetting of the retinal image occurs at the iris. However, it is suitable for imaging a smaller field of view at high resolution. It will be obvious to one skilled in the art of optical design that all of the aspects of the invention described herein for incorporating OCT into surgical microscopy of the anterior segment can be applied for narrow-angle retinal imaging as well, using this contact lens approach.

In some embodiments, an OCT unit may be connected to the viewing path of the surgical microscope 100 and/or the vitreoretinal viewing optics unit 200. For example, a beamsplitter may be used to direct a portion of light from the viewing path of the microscope 100 and/or vitreoretinal viewing optics unit 200 to an OCT unit. In some embodiments, the vitreoretinal viewing optics unit 200 is a BIOM3 adapter that optically delivers an inverted wide-angle (120 deg.) view of the retina to the image plane of the surgical microscope 100 by the use of a high-power non-contact lens (20D) and low-power reduction lens (F/200). However, any suitable vitreoretinal viewing adapter for visualizing the ocular fundus may be used, including a single reduction lens for visualizing the ocular fundus, such as contact lenses available from Volk Optical, Mentor, Ohio, U.S.A.

Although some embodiments are described herein with reference to sample arm scanners, it should be understood that a OCT, SDOCT, or SSOCT system may be used. An OCT system generally includes a light source, reference delay, optics for interfering the light returning from the sample scanner and reference delay. Optics for detecting and processing such interference light may be separately provided and attached to a microscope mounted OCT (MMOCT) scanner. Various techniques may be used to incorporate other(s) of these components within the MMOCT scanner housing (such as the reference delay or interferometer fiber coupler), and such various would be known to those skilled in the art of optoelectronics and are included within the scope of this invention.

Figure 2A:
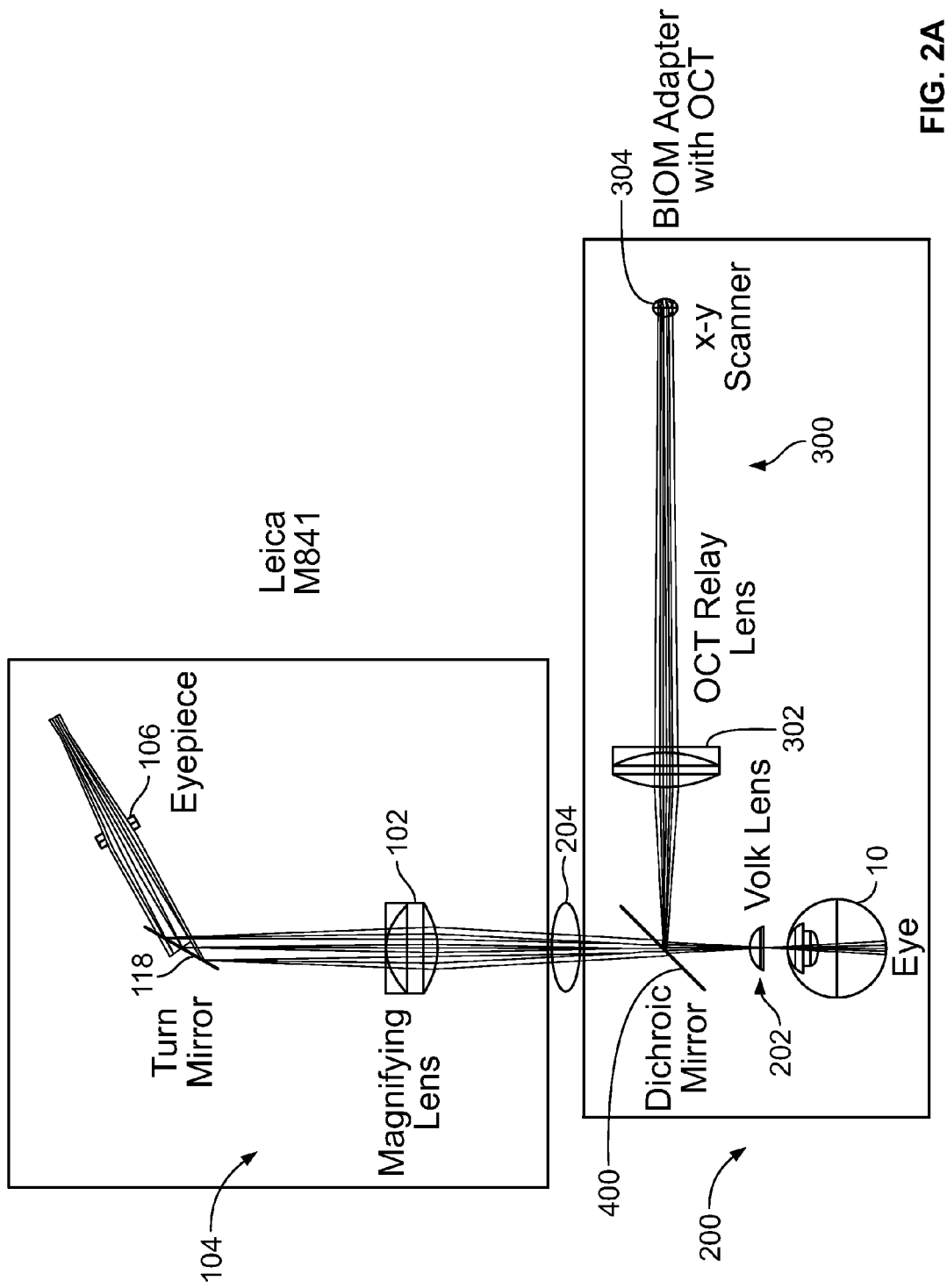
FIG. 2A is a schematic diagram of a microscope mounted optical coherence tomography (OCT) system according to some embodiments of the present invention.
Figure 2B:
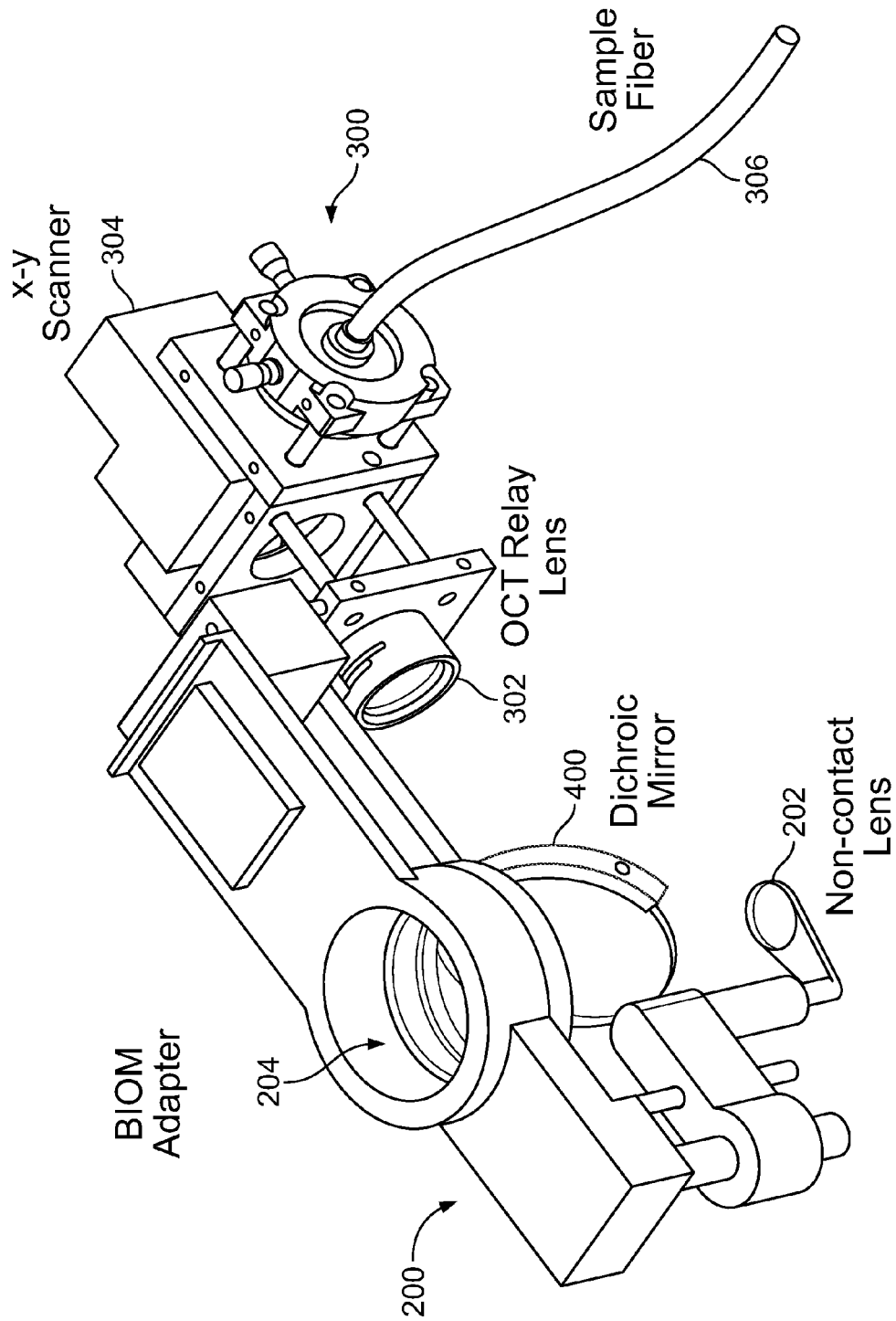
FIG. 2B is a perspective view of an OCT unit and a vitreoretinal viewing lens unit according to some embodiments of the present invention.

As illustrated in FIGS. 2A-2B, an OCT sample arm unit 300 according to some embodiments includes an OCT relay lens 302 and a scanner 304. A dichroic mirror or beamsplitter 400 is inserted between the lenses 202, 204 of the vitreoretinal viewing optics 200. Because the infinity-space of the surgical microscope 100 may not be readily accessible, the OCT beam is folded into the optical path of the surgical microscope between the non-contact lens 202 and the reduction lens 204. Without wishing to be bound by theory, the OCT beam may be focused through a high-powered (20D) wide-field non-contact lens 202, which acts as an ophthalmic lens, system resolution and FOV may be limited by the performance of this final optic, e.g., lens 202. The device includes scanners 304, such as a set of two-axis galvanometer scanners, and optics to scan the SDOCT beam across the retina of the patient through the non-contact lens 202.

In some embodiments, the system is designed to magnify the scanning SDOCT beam to accommodate for the demagnification introduced by the non-contact lens 202 to generally preserve lateral resolution, and the scan pivot is optically relayed to the patient's iris to ensure maximum FOV (FIG. 2A). For example, in some embodiments, the OCT relay lens 302 may include a beam forming unit for magnifying the OCT signal. The SDOCT beam is designed to be folded into the optical path of the surgical microscope 100 by using a dichroic mirror or beamsplitter 400 positioned between the non-contact and reduction lenses 202, 204 (FIG. 2B). The position of the beamsplitter 400 or fold mirror may reduce the optical foot-print under the BIOM3 adapter or vitreoretinal viewing optics 200 to avoid contact with the patient, thus setting physical constraints dictating the optical demagnification of the SDOCT beam onto the patient pupil. However, in this configuration, there may be advantages over imaging using a hand-held OCT system during surgery or SDOCT imaging through the microscope viewport by providing a stable imaging arm and avoiding optical losses by relaying the OCT beam through the surgical microscope optics.

Optical design simulations show a theoretical on-axis spots-size of 15 µm, a 24 µm off-axis spot-size for a 3 mm FOV, and a 32 µm off-axis spot-size for a 6 mm FOV for the configurations illustrated in FIGS. 2A-2B. These spot-sizes may be larger than those of conventional tabletop SDOCT scanners due to the high demagnification power of the non-contact lens 202 used to relay the SDOCT spot. The MMOCT was implemented using a current generation SDOCT engine with center wavelength at 841 nm and a FWHM bandwidth of 52 nm. Interferometric signals were captured using a 1024 pixel subset of a 2048 pixel line-scan camera (e2v, Ltd.). Custom software (Bioptigen, Inc., Durham, N.C. (U.S.A.)) performed real-time data acquisition, processing, archiving, and display. The SNR measured near DC was 108 dB with an axial resolution of 3.29 µm in tissue and a 6 dB falloff at 0.8 mm.

Figure 3:
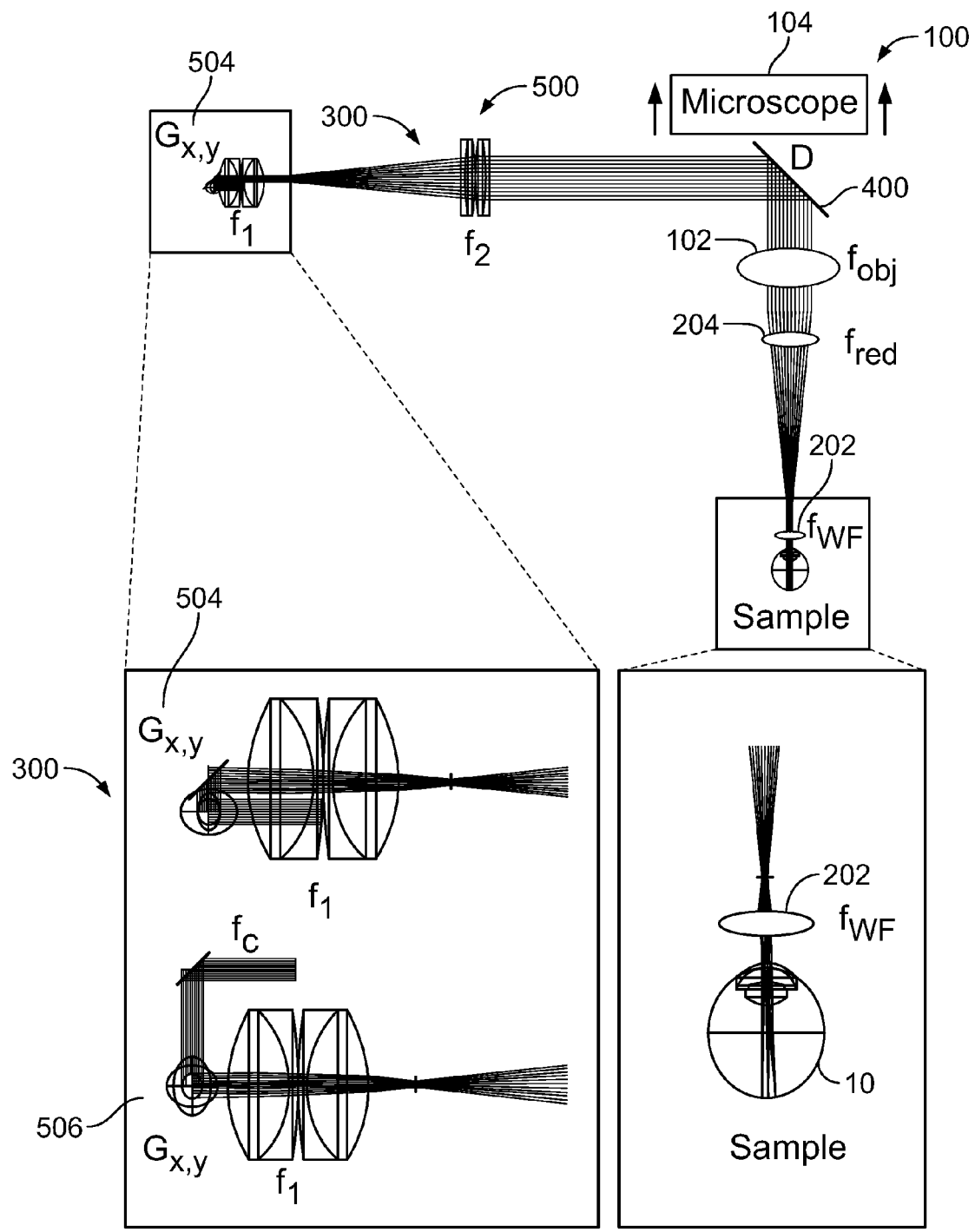
FIG. 3 is a schematic diagram of a microscope mounted optical coherence tomography (OCT) system according to some embodiments of the present invention.
Figure 5A:
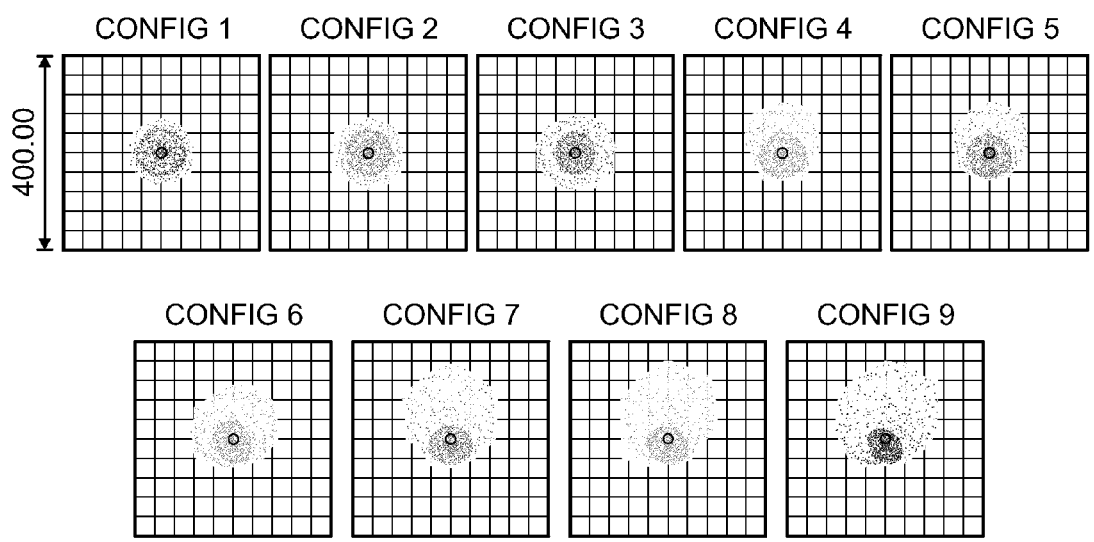
FIG. 5A illustrates spot size diagrams in microns across several scan position configurations using Zemax™ simulations of microscope mounted OCT according the configuration of FIG. 3.
Figure 5B:
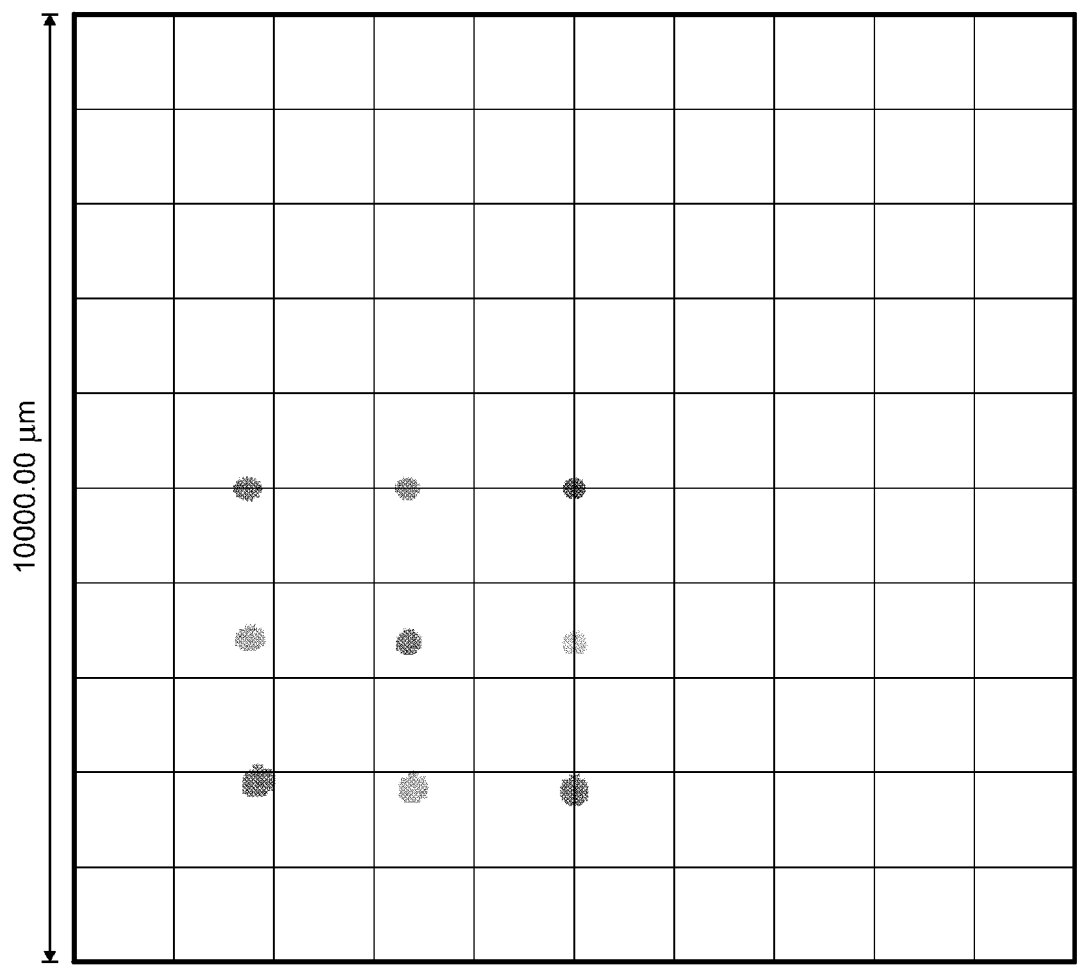
FIG. 5B is a field of view diagram with spots in microns corresponding to the respective spot sizes from FIG. 5A.
Figure 6B:
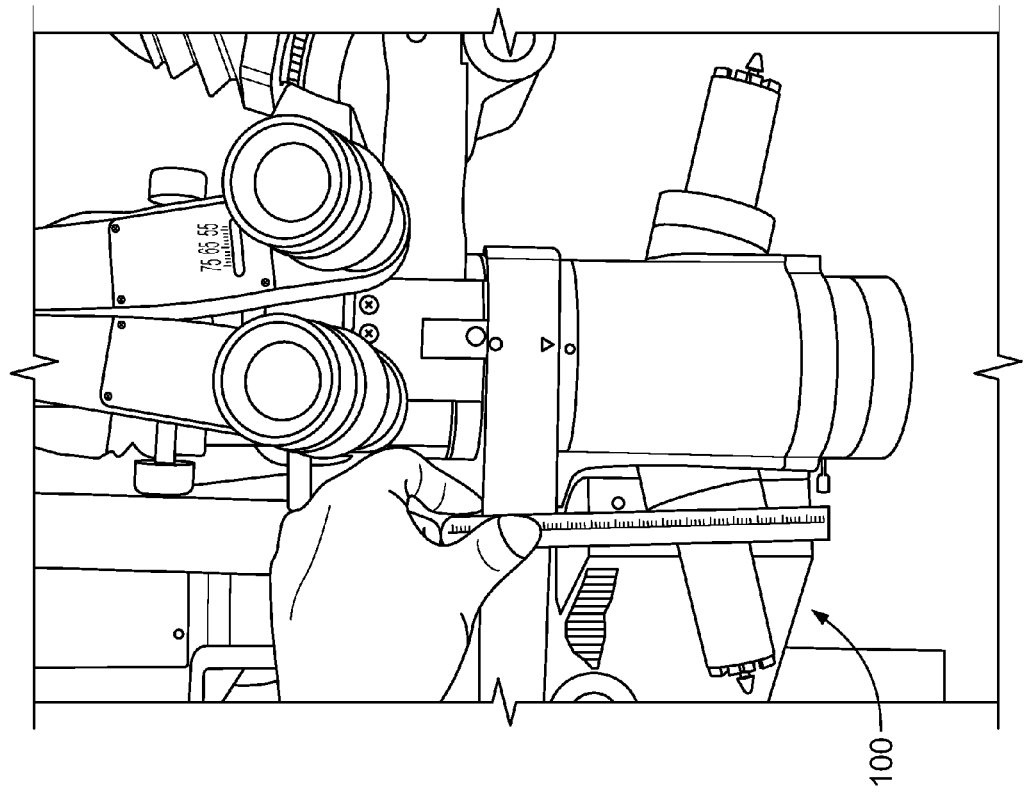
FIG. 6B is a front perspective view of the microscope of FIG. 6A.
Figure 6A:
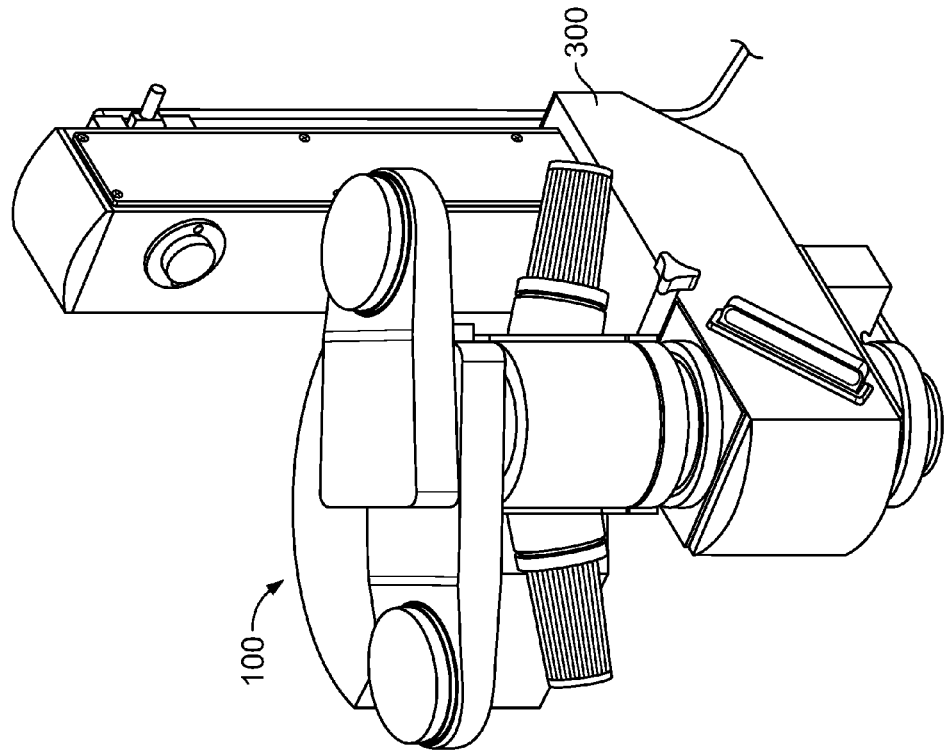
FIG. 6A is a front perspective view of a surgical microscope and microscope mounted OCT unit according to some embodiments of the present invention.
Figure 7:
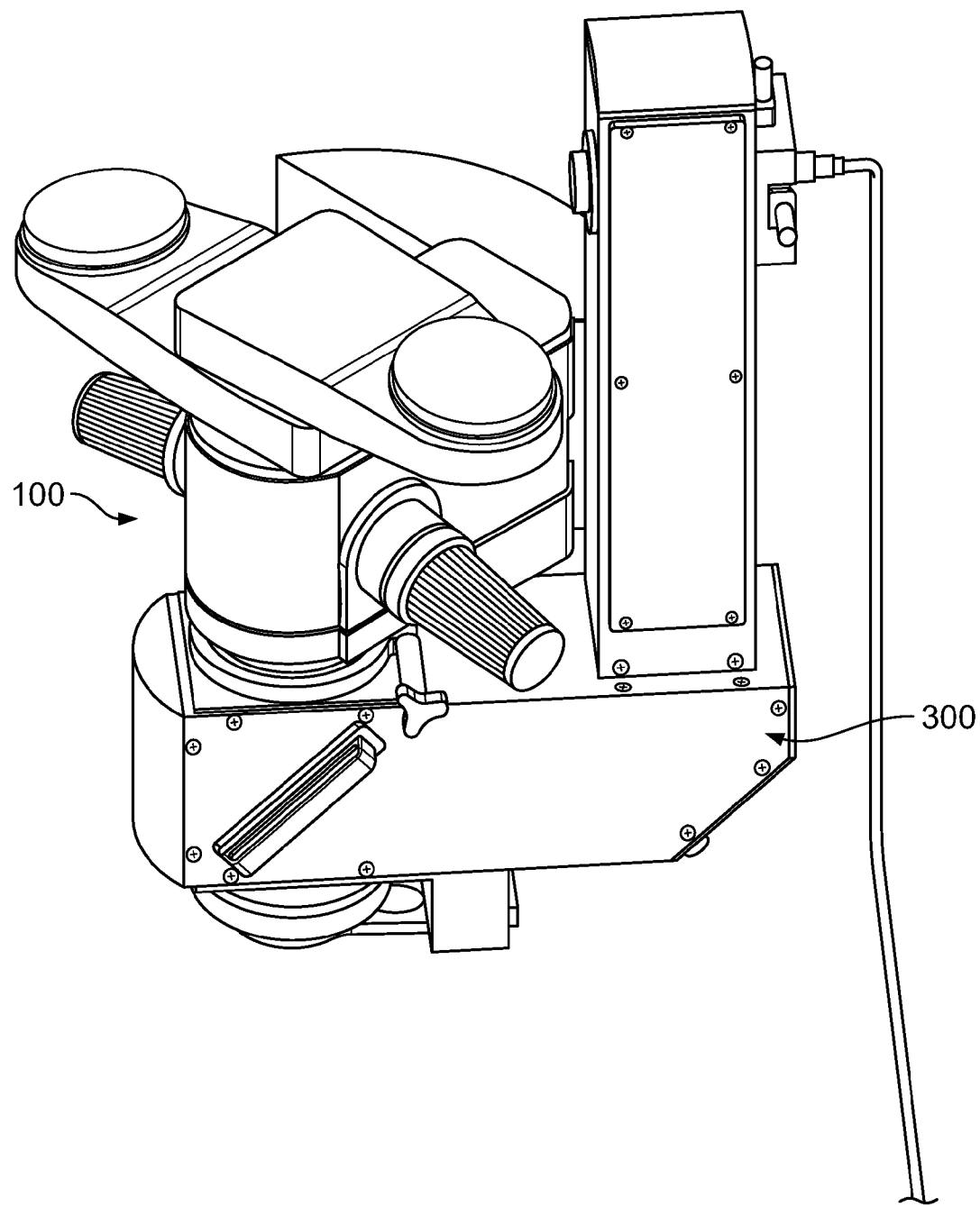
FIG. 7 is a side perspective view of a surgical microscope and microscope mounted OCT unit according to some embodiments of the present invention.
Figure 8A:
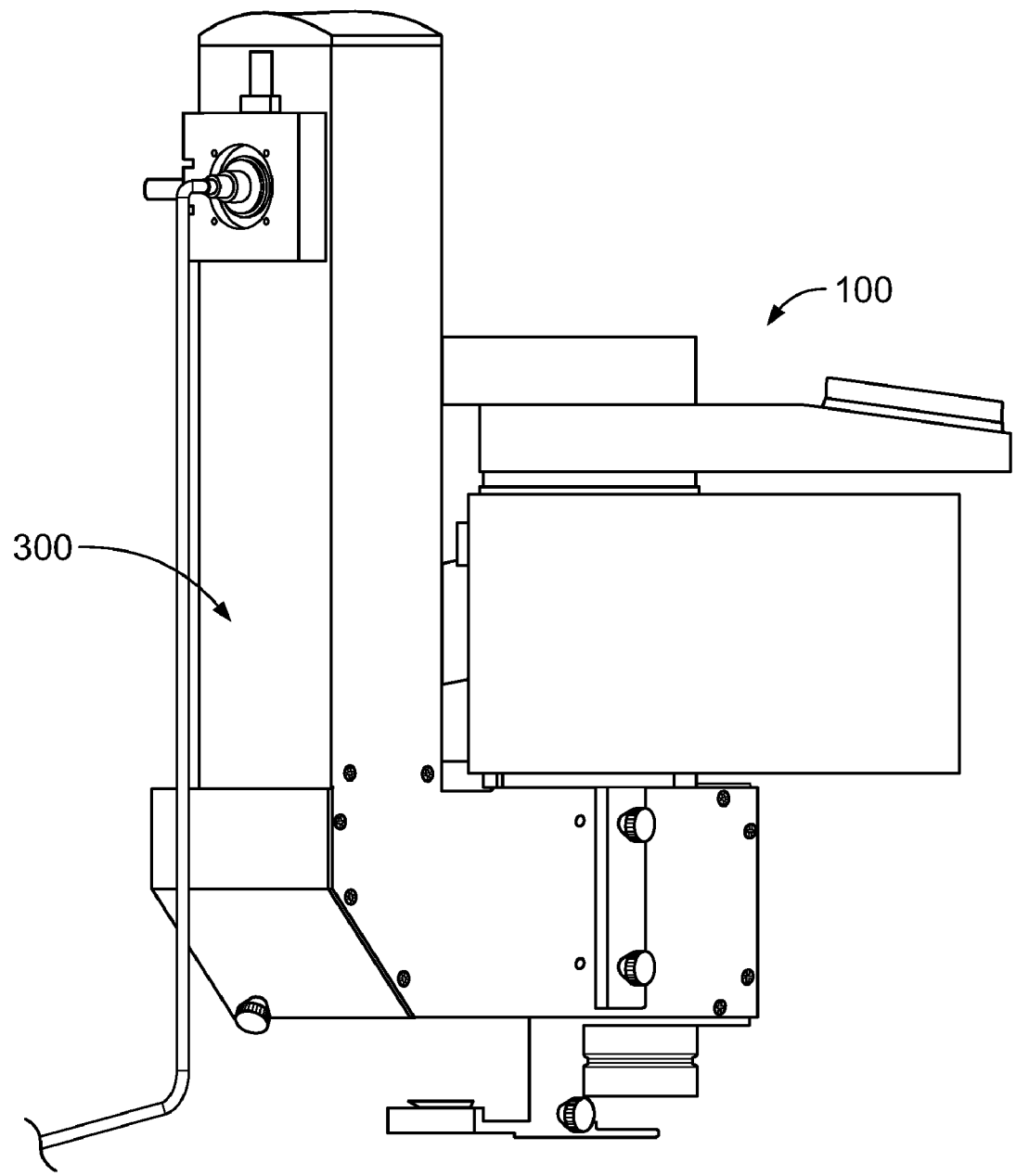
FIG. 8A is a back view of a surgical microscope and microscope mounted OCT unit according to some embodiments of the present invention.
Figure 8B:
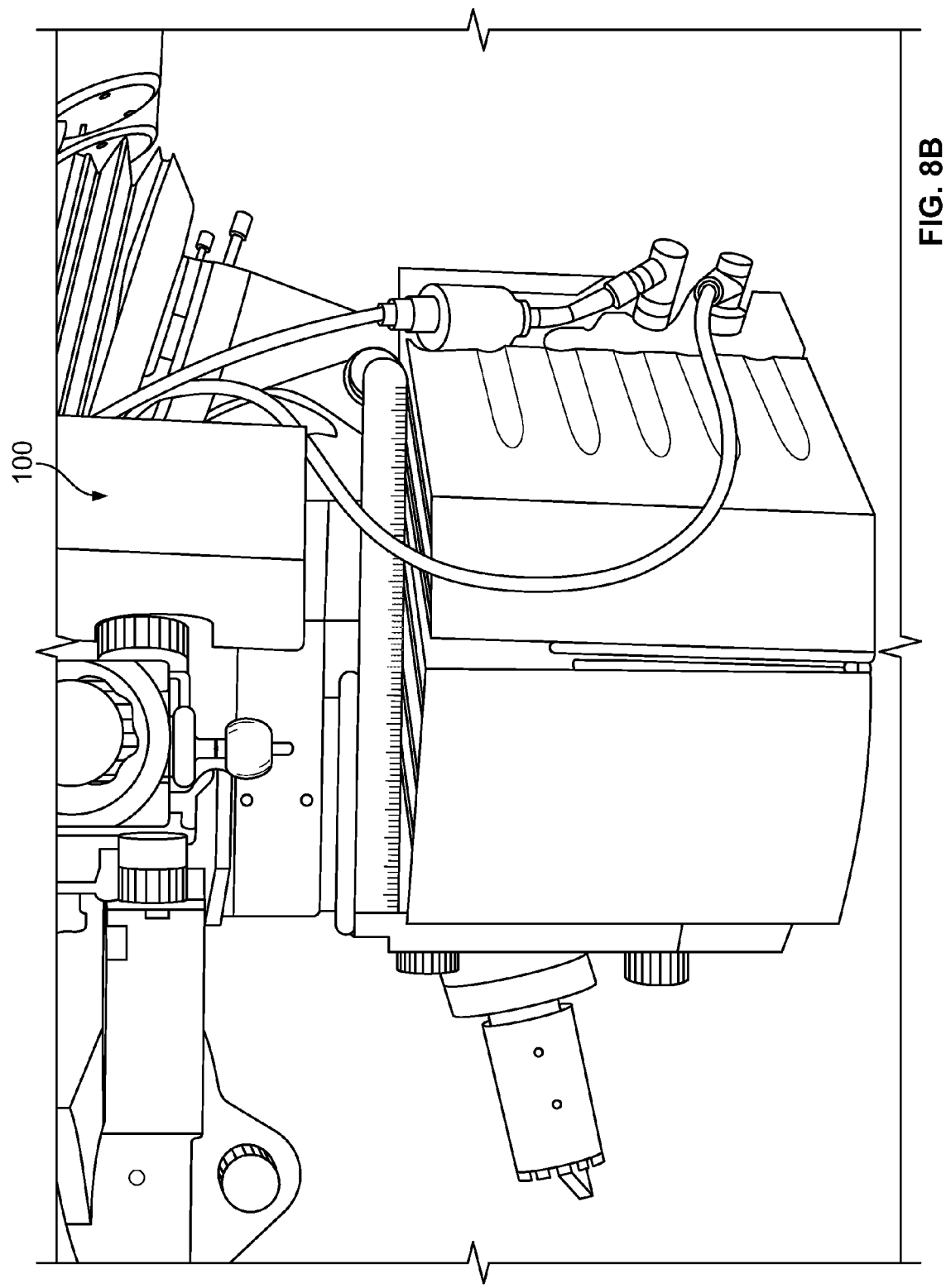
FIG. 8B is a back view of a surgical microscope of FIG. 8A.
Figure 9:
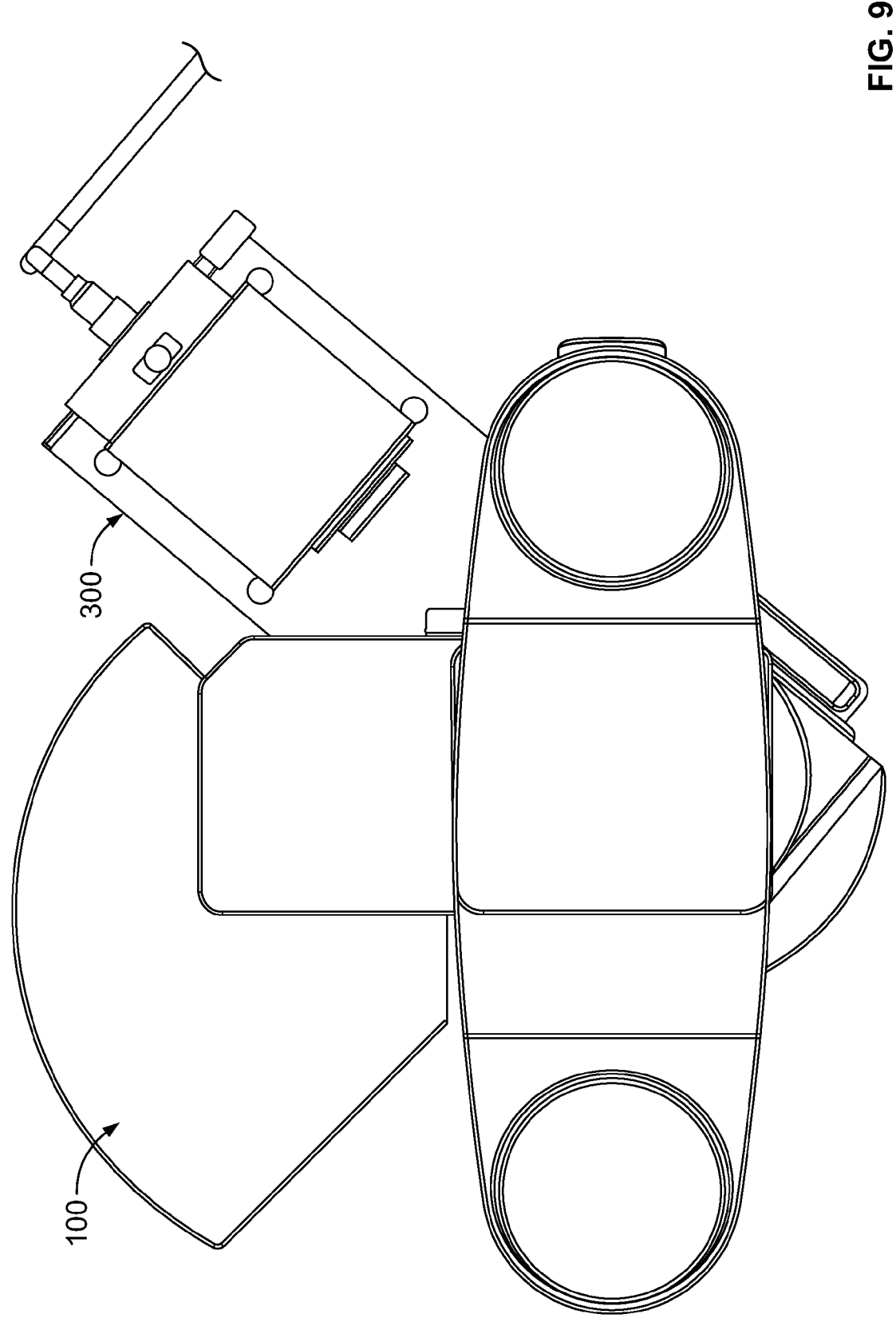
FIG. 9 is a top view of a surgical microscope and microscope mounted OCT unit according to some embodiments of the present invention.
Figure 10A:
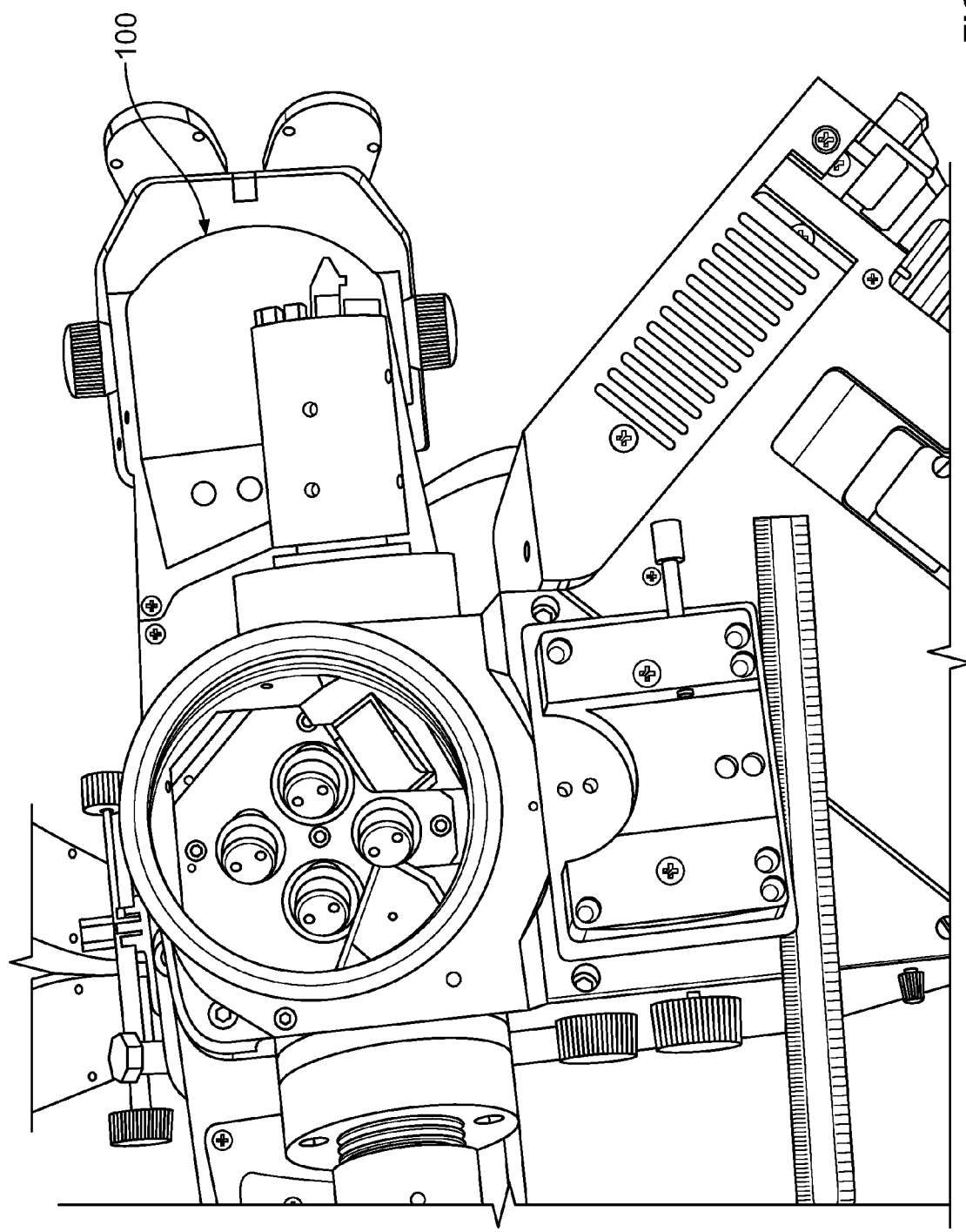
FIG. 10A is a bottom view of a microscope according to some embodiments of the present invention.
Figure 10B:
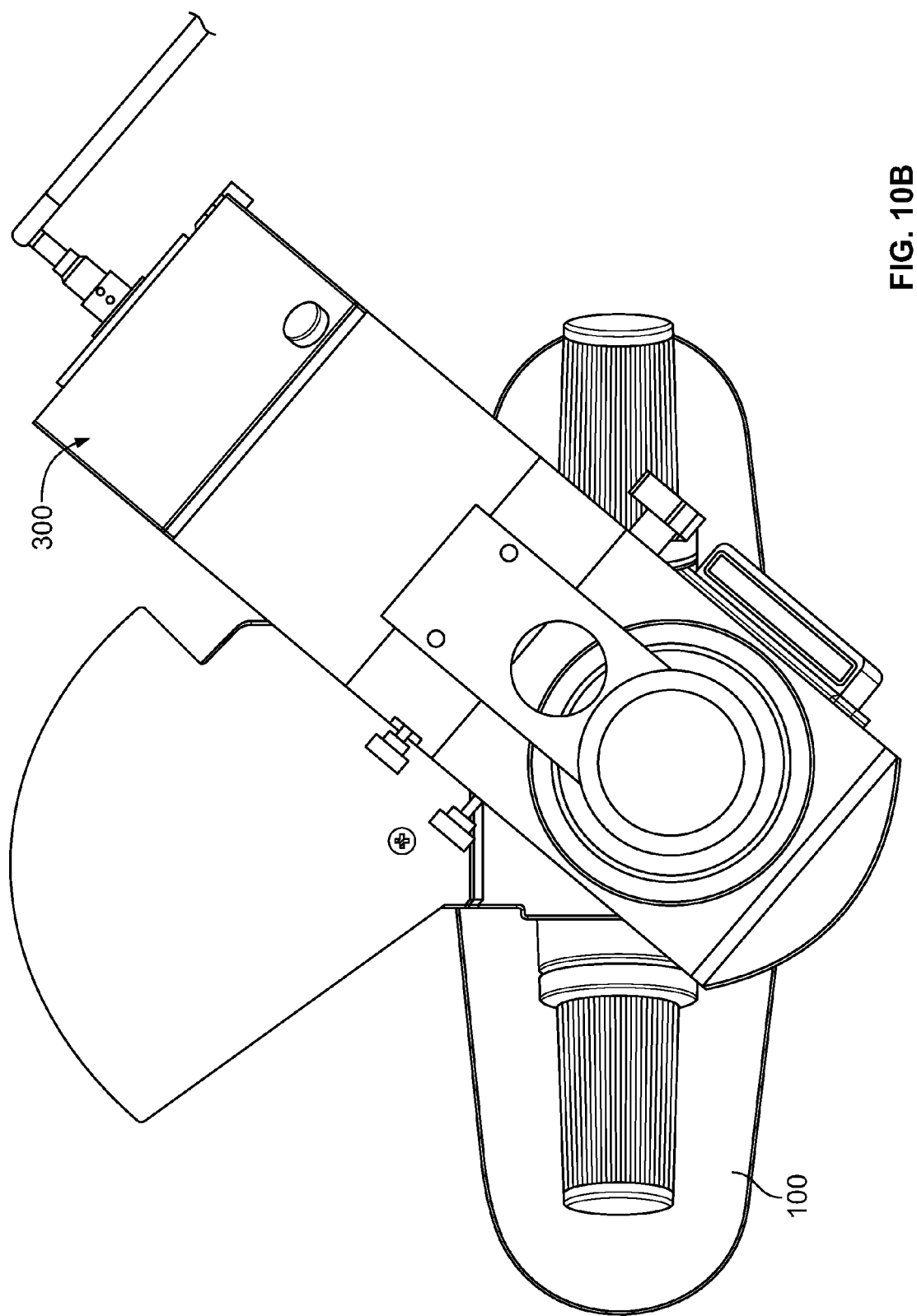
FIG. 10B is a bottom view of the microscope of FIG. 10A with an OCT unit attached according to some embodiments of the present invention.
Figure 11:
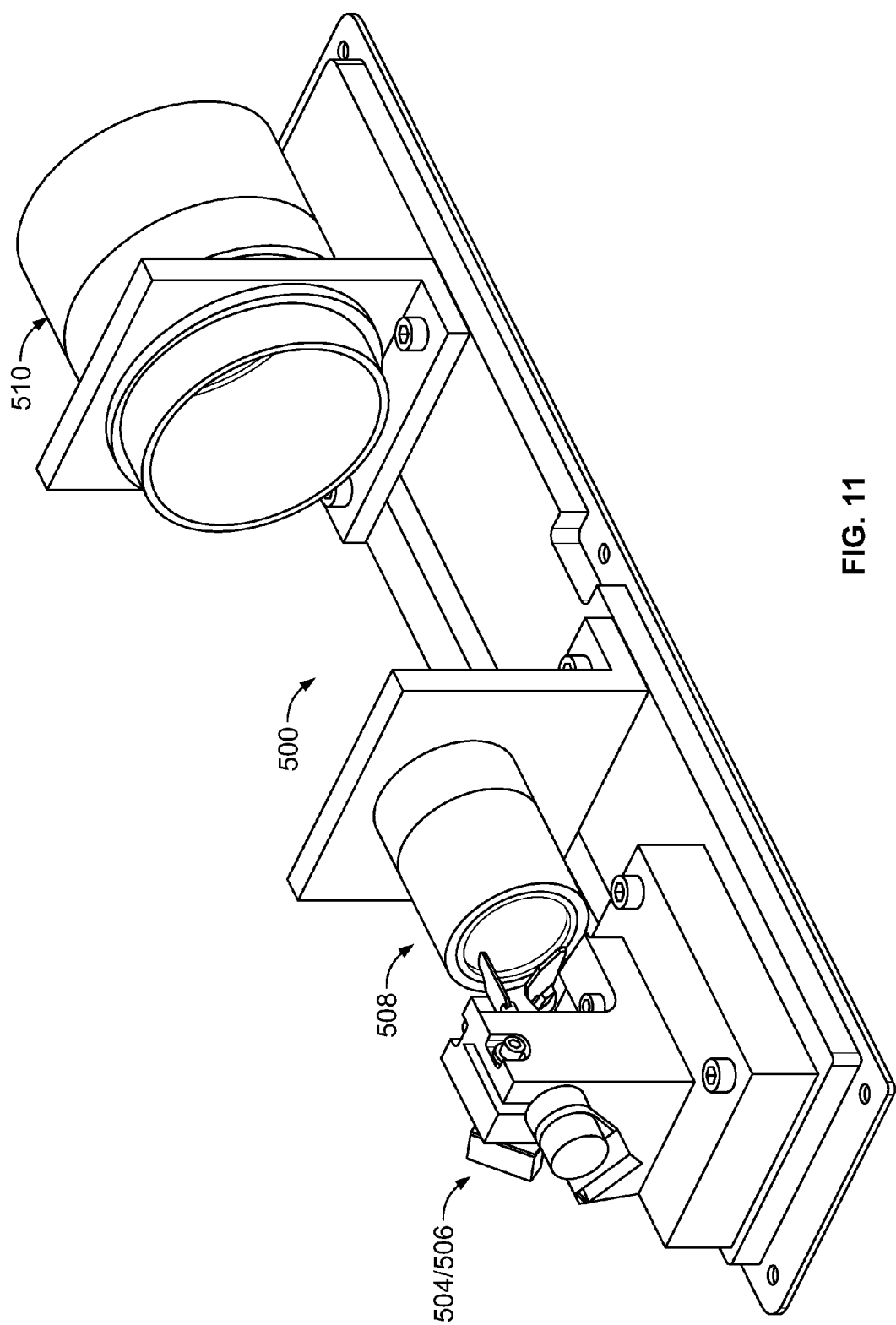
FIG. 11 is a perspective view of galvanometer scanners and a beam forming unit of an OCT unit according to some embodiments of the present invention.

Further embodiments of intraoperative MMOCT are illustrated in FIG. 3. As illustrated, the OCT scanner 300 includes a beamforming unit 500 having lens $f_1$ and $f_2$ and a scanner 504. The SDOCT illumination and collection paths are coupled to the imaging path of the ophthalmic surgical microscope via a dichroic element or beamsplitter 400 in the infinity space between the objective 102 and imaging optics 104 of the microscope 100. A collimated beam SDOCT illumination beam is scanned in two dimensions by a galvanometer pair, Gx,y (scanner 504) telecentrically relayed and expanded through f1 and f2, and combined with the surgical microscope 100 through dichroic mirror or beamsplitter 400. The SDOCT illumination beam is expanded so as to generally fill the entire back aperture of the surgical microscope objective 102. This may improve the spatial resolution of the MMOCT because the lens system including the objective 102, reduction lens 202, and widefield BIOM lens 204, act to demagnify the MMOCT illumination beam. The MMOCT illumination beam is magnified prior to coupling into the microscope path such that the collimated beam waist at the pupil of the eye is approximately 2 mm, thus preserving a 15 µm spot-size on the retina that is limited by the aberrations of the eye. Here, the dichroic mirror beamsplitter 400 is designed to transmit in the visible spectrum, so that the FOV and image quality through the imaging optics of the microscope remain unchanged. Optical simulations of this system as shown in FIG. 5 demonstrate an 8 mm FOV with FWHM spot-sizes ranging from 15 to 25 µm moving from on- to off-axis, respectively. The MMOCT was optically designed to work in conjunction with the optical path of an Oculus BIOM3 suspended from a Leica ophthalmic surgical microscope; however, any suitable microscope may be used. The surgical microscope is designed to image through a BIOM3 adapter for wide-field indirect ophthalmoscopy during vitreoretinal surgery. The BIOM3 optically delivers an inverted wide-angle (120 deg.) view of the retina to the image plane of the surgical microscope by the use of a high-power non-contact lens (90D) and low-power reduction lens (F/200). When positioned adjacent to the objective lens of the surgical microscope, the BIOM3 creates a high magnification optical telescope which relays a large FOV image of the fundus to the viewport of the surgical microscope 100.

The configuration illustrated in FIG. 3 acts as an intermediate coupler between the objective 102, reduction lens 202, and BIOM attachment 200, which are all attached to the bottom of the MMOCT device. This allows the second MMOCT design to be positioned clear of both the surgeon and patient as shown in FIG. 6-12. The configuration of FIG. 3 may also be securely attached to the microscope 100 at multiple positions, for example with components screwed into a microscope objective holder and attached to the bottom of the microscope, thus providing a stable optical path for the MMOCT.

Figure 13A:
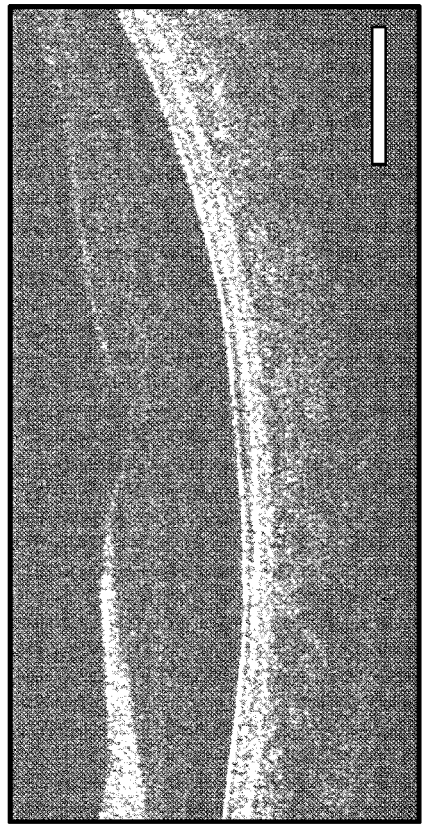
FIGS. 13A-13B are in vivo human retinal SDOCT data illustrating a fovea (FIG. 13A) and a fovea and optic nerve (FIG. 13B) acquired using an intraoperative SDOCT unit attached to a microscope according to some embodiments of the present invention. B-scans were acquired at 20 kHz line-rate with 1024×1000 pixels, an illumination power of 700 µW, and the scale bar is 0.5 mm.
Figure 13B:
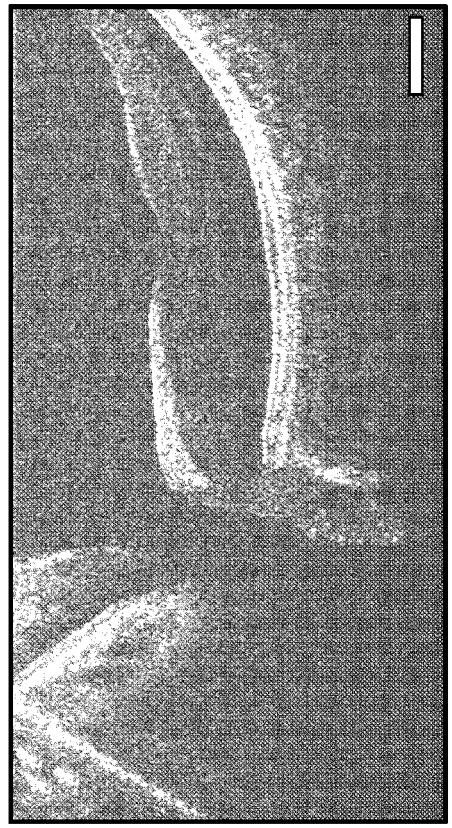
Figure 12A:
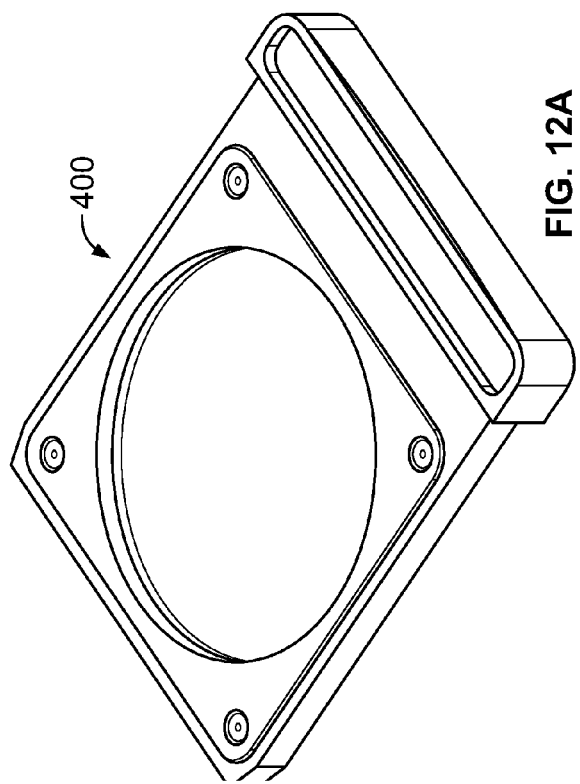
FIG. 12A is a bottom perspective view of a dichroic mirror that couples an OCT unit to a surgical microscope imaging path according to some embodiments of the present invention.
Figure 12B:
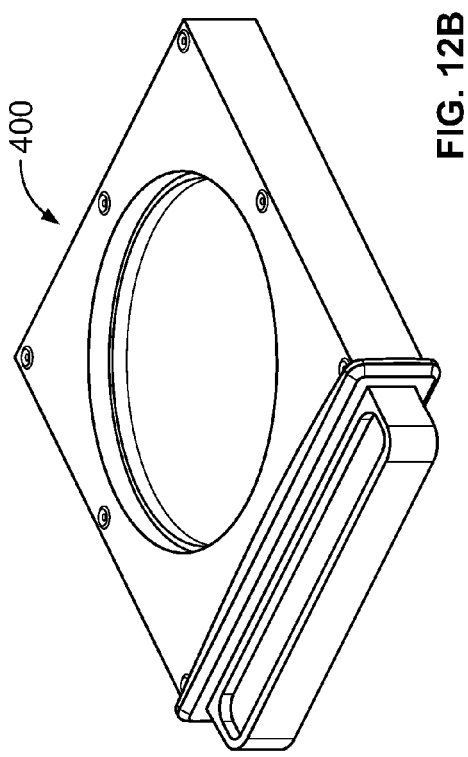
FIG. 12B is a top perspective view of the dichroic mirror of FIG. 12A.

In vivo human retinal SDOCT images were acquired using the MMOCT system design illustrated in FIG. 2 on a supine subject simulating the vitreoretinal surgery situation. Images were sampled at 20 kHz line rate with 1024×1000 pixels (axial×lateral) with 700 µW of illumination power at the pupil. Sequential B-scans were acquired with a 3 mm (FIG. 13A) and 6 mm (FIG. 13B) FOV, showing both fovea and optic nerve. Retinal images show structural resolution comparable to current generation tabletop SDOCT systems but with reduced SNR and contrast. This is likely a result of increased optical losses across the BIOM3 optics, which are optimized for visible wavelengths. Furthermore, the high magnification power of the BIOM3 non-contact lens caused some loss of back-scattered light outside of the acceptance angle of our SDOCT collection optics, thus reducing the intensity of the detected signal. The losses associated with the magnification of the BIOM and light collection efficiency are resolved in the alternative realization of the MMOCT of FIG. 3 by utilizing the objective lens of the surgical microscope as a collection optic.

Figure 4:
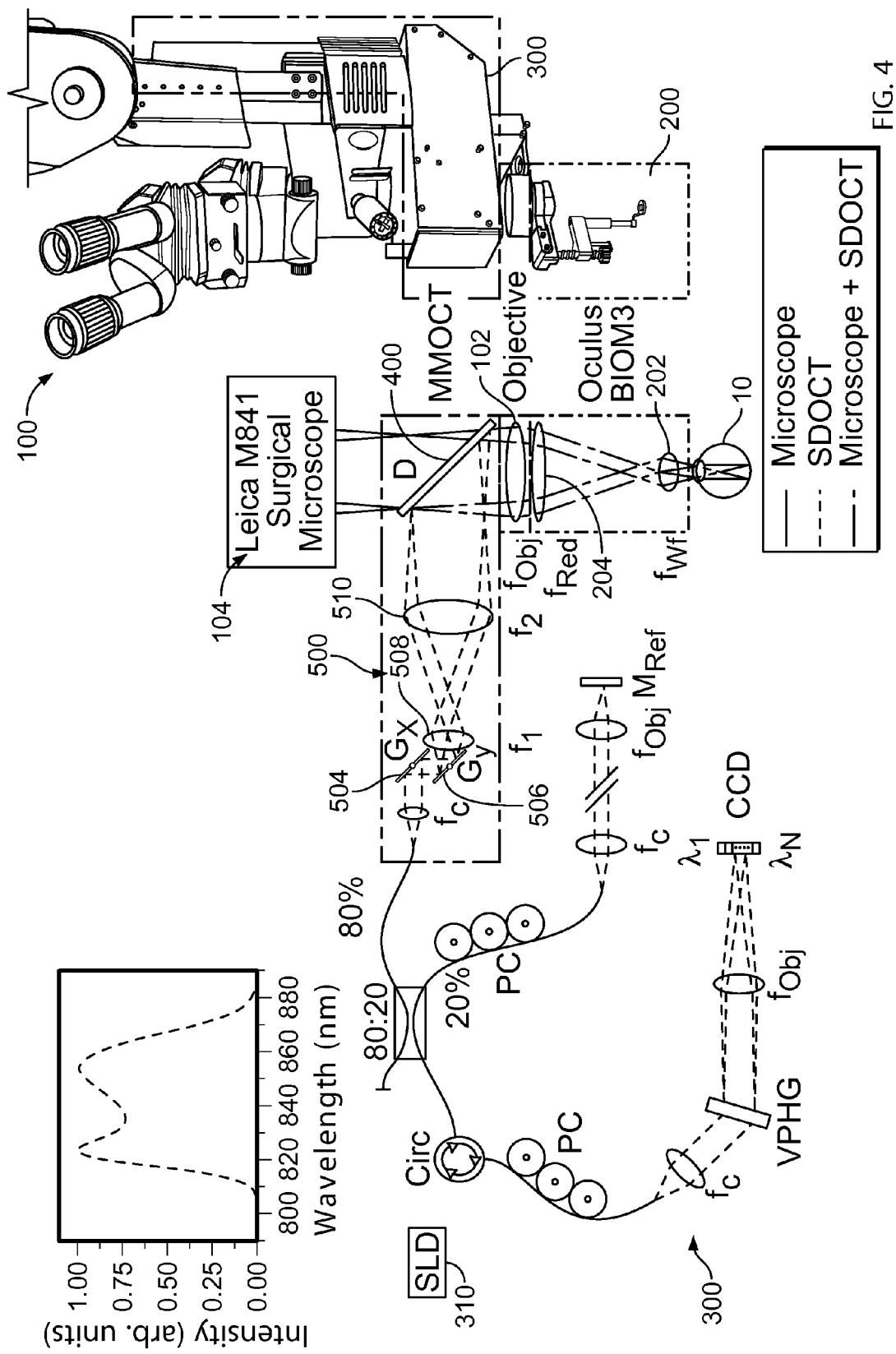
FIG. 4 is a schematic diagram of a microscope mounted optical coherence tomography (OCT) system according to some embodiments of the present invention.

The intraoperative MMOCT system illustrated in FIG. 3 was implemented as an attachment to a Leica M841 ophthalmic surgical microscope with a BIOM3 attachment as shown in FIG. 4. The OCT unit 300 includes an illumination source 310, such as a superluminescent diode, with a center wavelength of 840 nm and a bandwidth of 49 nm. The MMOCT sample arm included two-axis galvanometer scanners ($G_x$, $G_y$) 504, 506, a beam forming unit 500 including a 12.5× beam expander 508, 510($f_1$, $f_2$), and relay optics such as the beamsplitter 400, the microscope objective 102, and the reduction lens 204 (D, $f_{Obj}$, $f_{Red}$) to scan the SD-OCT beam, through the BIOM3 non-contact wide-field lens 202, across a 12 mm FOV on the retina of an eye 10 of the patient. The system illustrated in FIG. 4 was designed to magnify the scanning SD-OCT beam diameter to accommodate for the demagnification introduced by the BIOM3 (or vitreoretinal viewing optics 200) to preserve lateral resolution, and the scan pivot was optically relayed to the iris plane of the patient to ensure maximum FOV. The SD-OCT beam was designed to be folded into the optical path of the surgical microscope by using a dichroic mirror or beamsplitter 400 positioned in the infinity space of the surgical microscope 100, between the objective lens 102 and beamsplitter and imaging optics of the microscope 104. The position of this fold mirror or beamsplitter 400 was chosen to reduce the optical foot-print under the BIOM3 adapter to avoid contact with the patient. Here, sharing the objective lens 102, reduction lens 204, and wide-field non-contact lens 202 between the OCT and microscope optical paths allowed for a common focal plane between the two modalities, which could be adjusted together by changing the axial position of the wide-field lens 202.

The configuration shown in FIG. 4 may provide a stable imaging arm; however, since the OCT is relayed through the microscope objective 102, reduction 204, and high-powered (90D) wide-field non-contact lenses 202, the lateral resolution and FOV of the OCT are limited by the performance of these optics at 840 nm. Interferometric signals were captured using a 1024 pixel subset of a 2048 pixel line-scan CCD camera (SM2CL2014-e2v, Ltd.). Custom software (Bioptigen, Inc.) performed real-time data acquisition, processing, archiving, and display. Using 700 µW of illumination power at the sample, the SNR measured near DC from an ideal reflector was 112 dB with an axial resolution of 6.51 µm in air, 6 dB falloff at 1.45 mm, and total axial range of 2.24 mm.

Optical design simulations (ZEMAX) of the MMOCT, using a Pomerantzef model eye (O. Pomerantzeff, H. Fish, J. Govignon, and C. L. Schepens, Ann Ophthalmol 3, 815-819 (1971)) as the sample, vendor-provided lens models for the MMOCT relay optics, and paraxial approximations for the microscope objective and BIOM3 lenses, yielded theoretical FWHM spot-sizes of 10 µm over a 12 mm FOV. The lateral resolution was then evaluated experimentally by measuring the optical transfer function (OTF) and subsequently calculating the point spread function (PSF) at the focal plane as shown in FIG. 14A-14C. The OTF was measured experimentally by acquiring a series of images of a USAF 1951 test chart, positioned at the focal plane of a model eye, consisting of a 40D focusing objective and adjustable iris. The lateral OTF cross-section was then calculated using the normalized contrast of each group of elements (FIG. 14A), and the respective PSF cross-section was calculated from the Fourier transform of the OTF (FIG. 14B). Finally, lateral cross-sections of the measured lateral PSF function was compared with theoretical values for confocal and wide-field imaging systems, as well as values simulated using ZEMAX (FIG. 14C). For an illumination beam diameter of 2.5 mm at the pupil, these PSFs showed FWHM resolutions of 16, 12, 34, and 16 µm for the measured, theoretical confocal, theoretical widefield, and ZEMAX simulated values, respectively. The theoretical lateral PSF at the focal plane of a confocal system is described by $I(v)=[2J_1(v)/v]^4$. T. Wilson, Confocal microscopy (Academic Press, London; San Diego, 1990). Here, $v=(2\pi/\lambda)r \sin(\alpha)$, where r is the radial position and $\alpha$ is the half-angle subtended by the objective. The measured lateral PSF cross-sections were well correlated with theoretical and simulated values, and demonstrated a confocal resolution improvement when compared with the theoretical PSF cross-section for wide-field imaging. These theoretical lateral resolution limits, however, will ultimately be dominated by the confocal focused spot size and aberrations present in the eye.

Figure 14D:
FIG. 14D is an image of ten co-registered and averaged image excerpts from a video of 8×1.75 mm (lateral×depth) B-scans of in vivo human macula (Media 1). Images were acquired with 1024×1024 pixels (lateral×spectral) at a frame-rate of 20 Hz with an illumination power of 700 µW. The scale bar is two degrees.

In vivo human fundus was imaged using the MMOCT with 700 µW illumination power at the pupil to demonstrate image quality over an 8 mm FOV (FIG. 14D). Degradation of lateral resolution at the edges of the image may be attributed to beam quality nonuniformity associated with scanning across the aspheric high-powered (90D) wide-field non-contact ophthalmic lens. Human images were acquired in accordance with a protocol approved by the Duke University Health System Institutional Review Board. All subjects were imaged in the supine position, without pupil dilation and any contact with the eye. MMOCT alignment and aiming was accomplished using the foot pedal controlled articulating arm of the surgical microscope, simulating intraoperative operation. All images were acquired with 1024×1024 pixels (lateral×spectral) at 20 kHz line-rate for continuous imaging at 20 Hz frame-rate. Ten of these frames were then co-registered and averaged for improved SNR and speckle reduction in post-processing.

Figure 20A:
FIG. 20A-20C are microscope mounted OCT (MMOCT) in vivo images of human macula. Ten co-registered and averaged images were exerpt from videos of 4.7×1.5 mm B-scans of a healthy human fovea (FIG. 20A) and optic nerve (FIG. 20B).
Figure 20B:
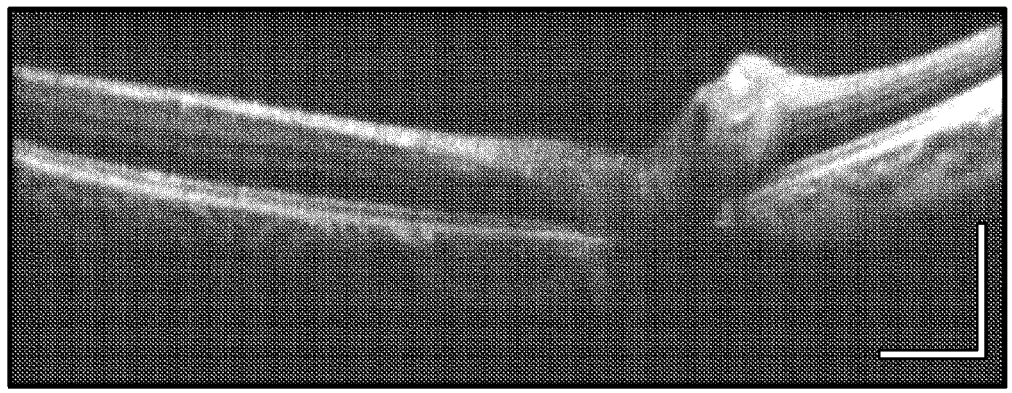
Figure 20C:
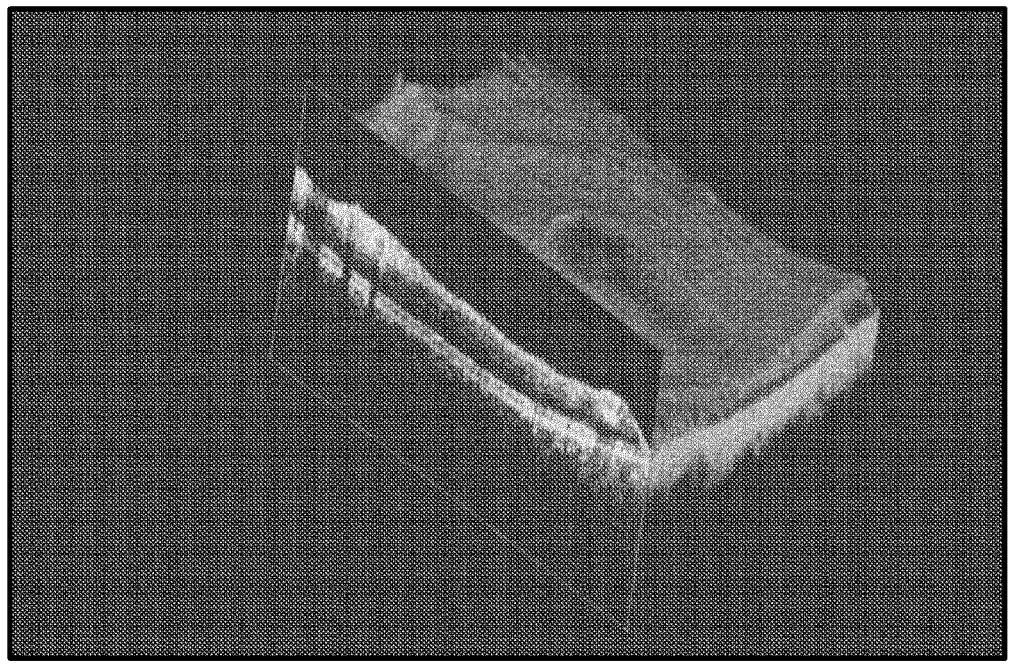

Densely sampled images of both healthy human fovea (FIG. 20A) and optic nerve (FIG. 20B) were acquired in vivo with 1024×1024 pixels (lateral×spectral) over a 4.7 mm lateral FOV at 20 kHz line-rate. Ten of these frames were co-registered and averaged for improved SNR and speckle reduction to demonstrate the lateral and axial resolution of the MMOCT. Here, the structure and vasculature at the foveal pit and optic nerve were visualized with high contrast, showing both retinal tissue layers and chorodial structure. Finally, a large 8×8 mm FOV volumetric dataset of the macula was acquired with 200 B-scans of which, each B-scan was sampled at 1024×1024 pixels (lateral×spectral) (FIG. 20C). Sequential B-scans were co-registered to remove interframe bulk motion artifacts and the dataset was displayed as a volumetric rendering using Amira (Visage Imaging, Inc.) in post-processing.

Figure 21B:
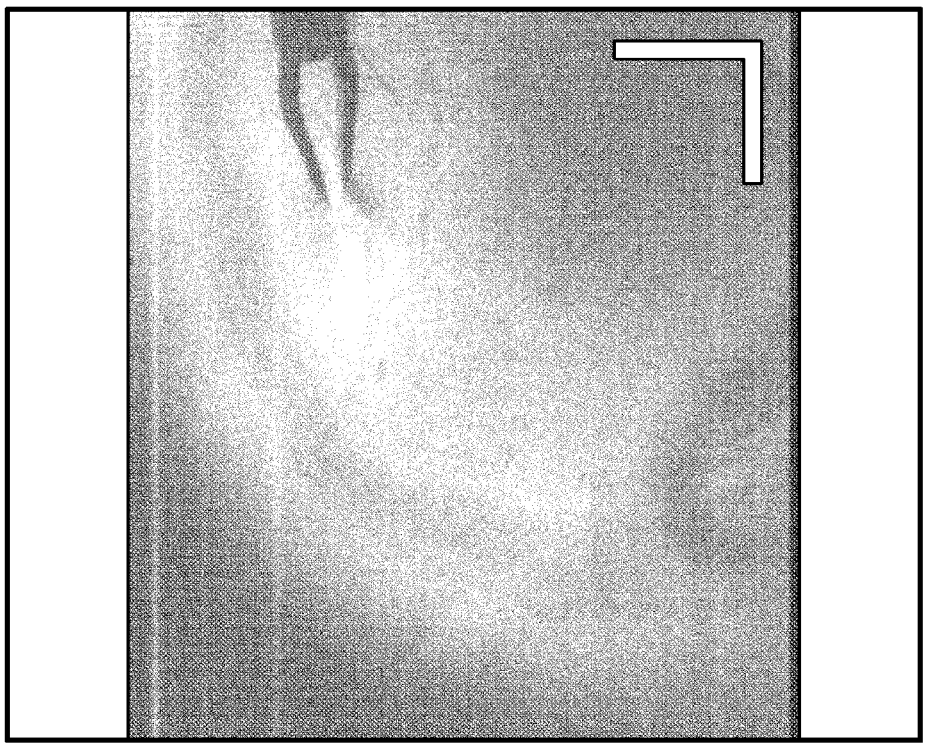
FIGS. 21A-21B are images of MMOCT surgical manipulations in cadaveric porcine eyes. Vitreoretinal surgery was simulated by performing procedures through an ophthalmic surgical microscope (FIG. 21A). 6×6 volumetric datasets were acquired using the MMOCT concurrently with surgical manipulations (FIG. 21B). The SVP shows the forceps pinching the retinal membrane. The illumination power is 700 µW. The scale bar is 2 degrees.
Figure 21A:
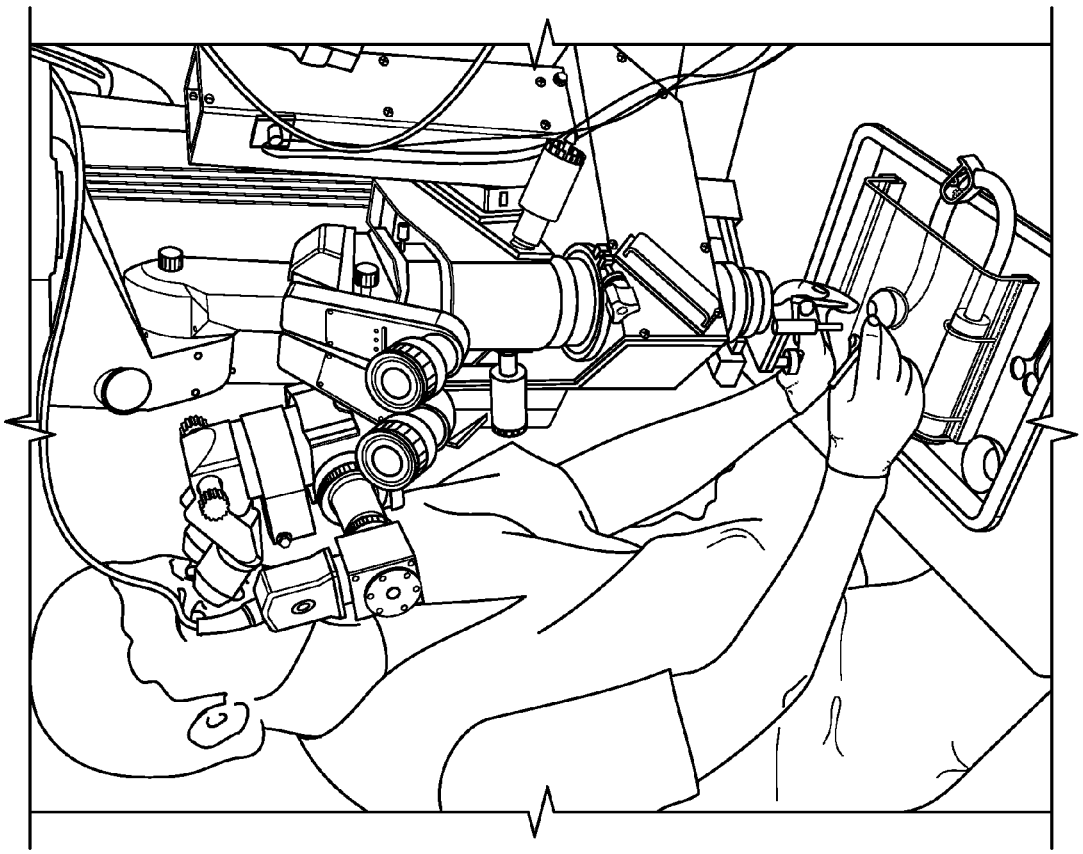

Vitreoretinal surgery was simulated by performing procedures, through an ophthalmic surgical microscope, on cadaveric porcine eyes. A fiber-optic light pipe was used as the illumination source and the porcine retina was manipulated using standard vitreoretinal surgical instruments. MMOCT volumes over a 6×6 mm FOV were acquired, concurrently with surgical procedures, to demonstrate visualization of instrument-tissue interactions (FIGS. 21A-21B). All volumetric datasets were acquired with 500 B-scans, sampled with 1024×500 pixels (spectral×lateral) at 20 kHz line-rate and an illumination power of 700 µW at the pupil. Wetting drops were applied to the pupil during imaging to maintain the optical transparency of the cadaveric eye.

Figure 15A:
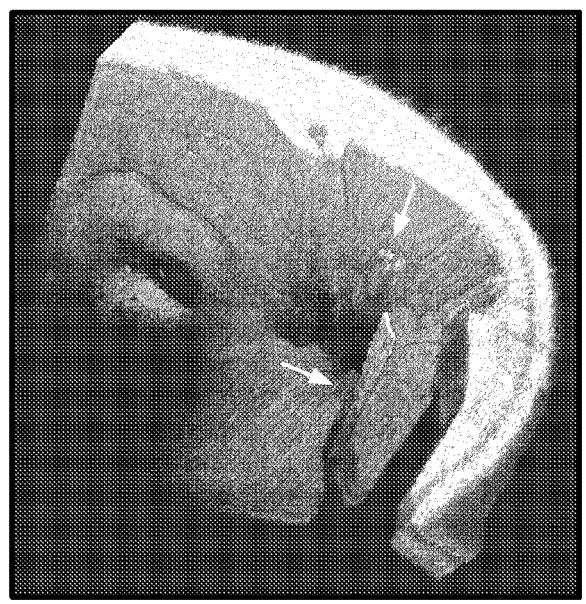
FIGS. 15A-15B are images acquired using microscope mounted OCT during surgical manipulation in an cadaveric porcine eye. The surgical procedure was performed by viewing through the surgical microscope, simulating vitreoretinal surgical conditions, and with concurrent acquisition of microscope mounted OCT volumes. The porcine retina was illuminated using a fiber-optic light an dmanipulated using forceps. A 6×6 mm volumetric dataset was aquired with 500 B-scans, sampled with 1024×500 pixels (spectral×lateral) at a 20 kHz line rate.
Figure 15B:
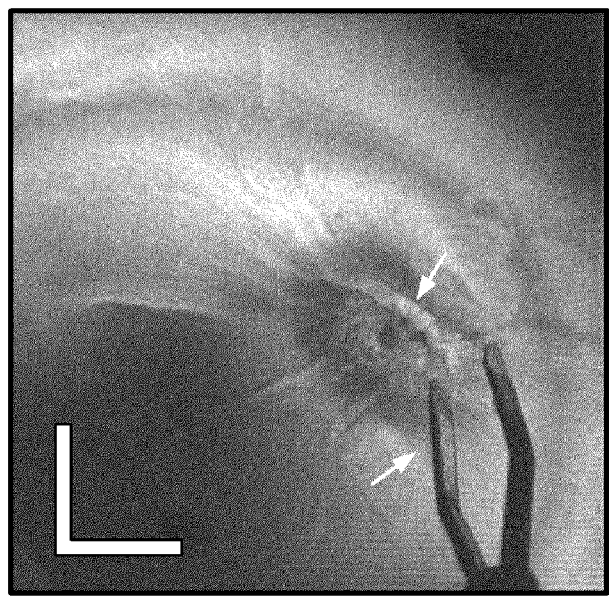

The porcine retina was illuminated using a fiber-optic light pipe and manipulated using vitreoretinal surgical forceps. The retina and surgical instruments were visible through conventional viewing through the pupil via the microscope. The volumetric rendering (FIG. 15A) and summed-voxel-projection (SVP) (FIG. 15B) allow for the MMOCT visualization of both the instrument (arrow) and a piece of glial tissue extruding from the optic nerve (arrow). The volume rendering shows that the tissue below the forceps is obscured by shadows (FIG. 15A), and most of the instrument is not visible because the polished metal edges of the forceps specularly reflect the OCT light outside of the collection aperture of the MMOCT. However, the structure and orientation of the forceps can clearly be visualized on the SVP (FIG. 15B). MMOCT visualization of surgical tools may be enhanced by artificially creating scattering surfaces, such as by roughening the flat faces of instruments. Sequential B-scans were co-registered to remove interframe bulk motion artifacts and the dataset was displayed as a volumetric rendering using Amira (Visage Imaging, Inc.) in post-processing.

Figure 22:
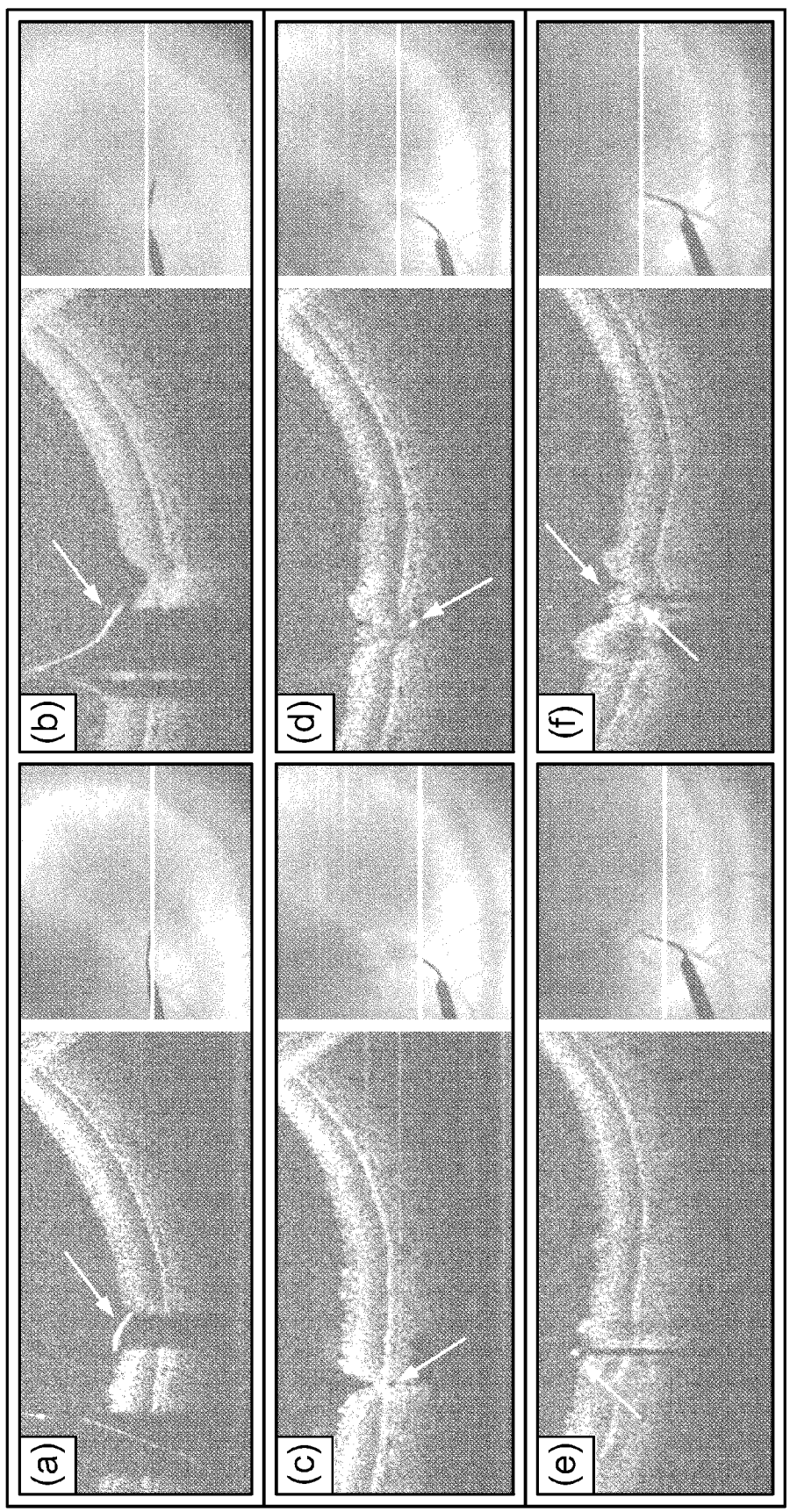
FIGS. 22A-22F are illustrations of retinal vessel cannulation in a cadaveric porcine eye. Three volumetric datasets were acquired using the MMOCT with a SR needle above the retina prior to cannulation (FIGS. 22A-22B), penetrating the subretinal space (FIGS. 22C-22D), and successfully cannulating a retinal vessel (FIGS. 22E-22F). Two B-scans, corresponding to locations indicated by the white line on the SVP, are shown from each volumetric dataset to demonstrate instrument-tissue interactions along different positions of the needle.

Retinal vessel cannulation in the cadaveric porcine eye was performed through the surgical microscope and imaged concurrently using the MMOCT. A series of three volumetric datasets were acquired with a subretinal (SR) needle above the retina prior to cannulation (FIGS. 22A-22B), penetrating the subretinal space (FIGS. 22C-22D), and successfully cannulating a retinal vessel (FIGS. 22E-22F). Two B-scans, corresponding to locations indicated by the white line on the SVP, are shown from each volumetric dataset to demonstrate instrument-tissue interactions along different positions of the needle. When the SR needle was above the retina, the MMOCT B-scan (FIG. 22A) showed shadowing of the underlying tissue along the length of the needle (arrow). Furthermore, in the nonvitrectomized porcine eye, the B-scans showed retinal tissue compression by the vitreous near the tip of the instrument (FIG. 22B). The MMOCT B-scans also allowed for visualization of depth cross-sections of the needle (blue arrow) as it penetrated the subretinal space (FIGS. 22C-22D). Finally, cannulation of a retinal vessel was confirmed by the MMOCT as B-scans, perpendicular the axis of the needle, showed cross-sections of the instrument tip (arrow) enter the lumen of the vessel (arrow) (FIGS. 22E-22F).

Figure 23:
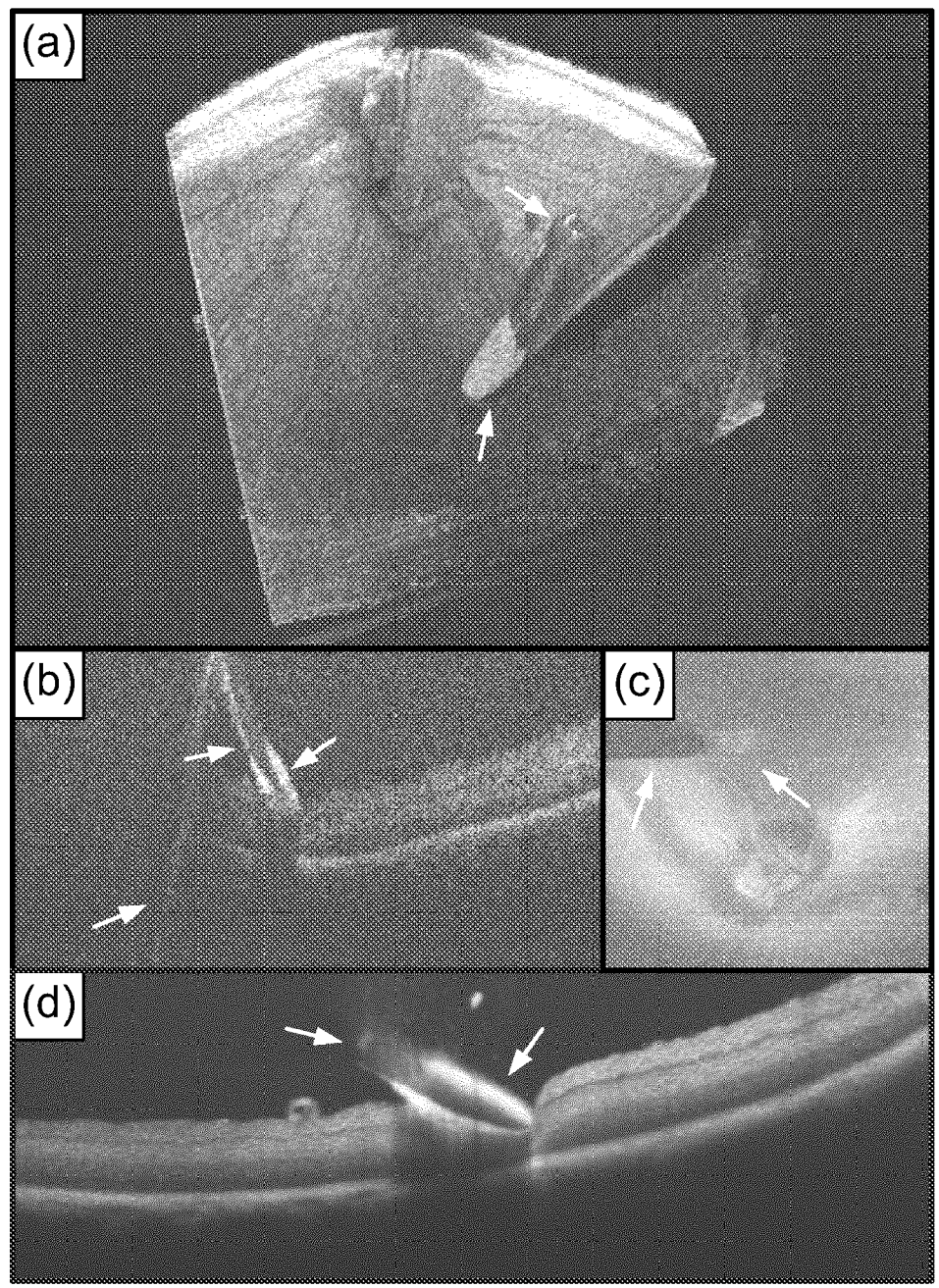
FIGS. 23A-D are MMOCT images of membrane scraping in a cadaveric porcine eye according to some embodiments.

Membrane scraping in the cadaveric porcine eye was imaged using MMOCT. A volumetric dataset was acquired using the MMOCT with a Tano Diamond Dusted Membrane Scraper (DDMS) compressing the retina. The volume rendering of the instrument-tissue interaction (FIG. 23A) shows the brightly scattering diamond dusted tip (bottom arrow) and opaque holder (top arrow) of the DDMS near the optic nerve. The B-scan (FIG. 23B), corresponding to the location indicated by the white line in the SVP of the dataset (FIG. 23C), shows compression of the top retinal layer by the tip of the DDMS. Also, the soft silicone body of the DDMS (top left arrow) is shown, attached to the opaque holder (bottom left arrow—conjugate image folding over), and is partially optically clear. Ten co-registered and averaged B-scans of retinal tissue compression using the DDMS (FIG. 23D) confirms that the soft silicone body of the instrument (top left arrow) is partially optically transparent at MMOCT wavelengths.

Figure 16:
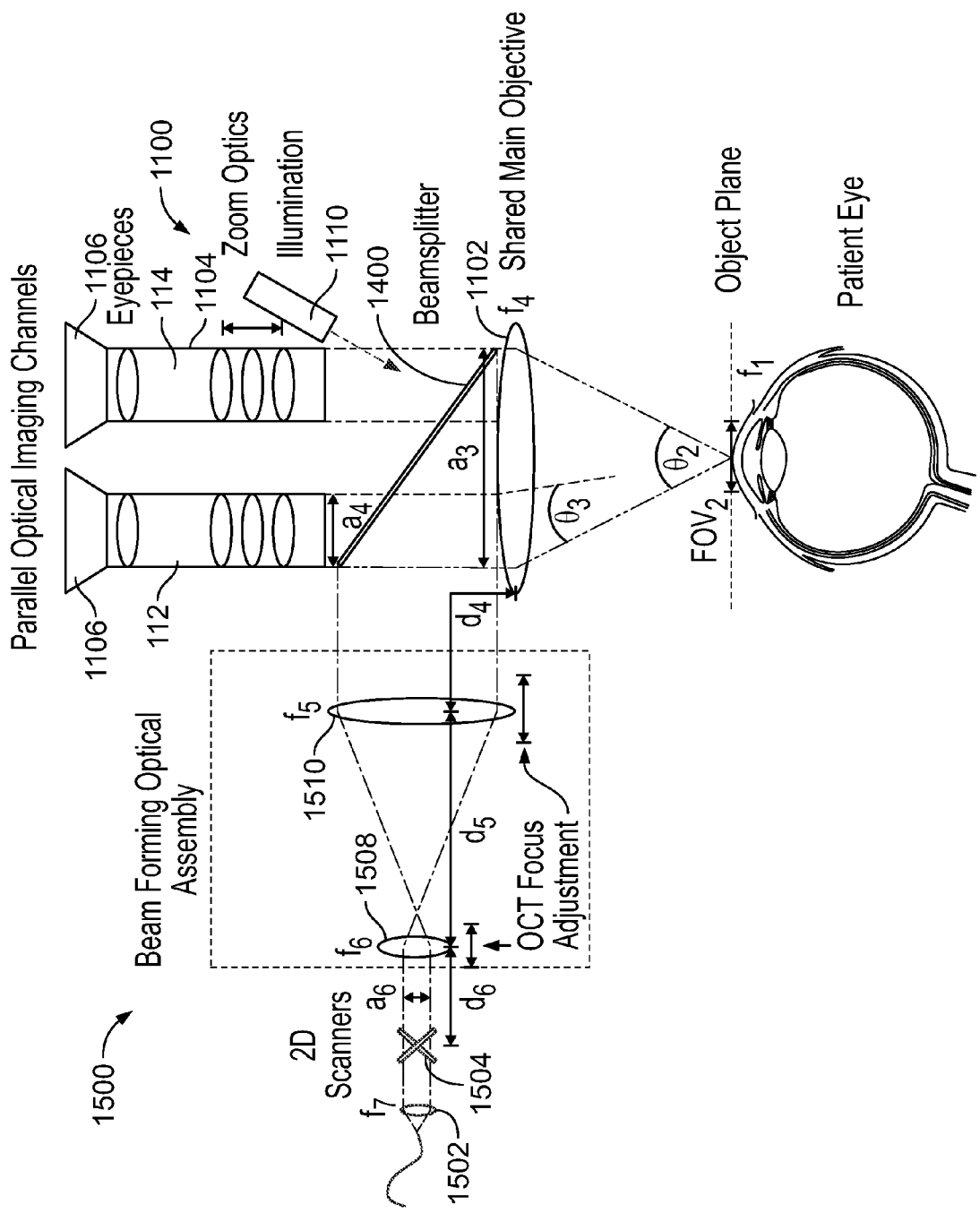
FIG. 16 is a schematic diagram illustrating an OCT scanner and beam forming assembly coupled to the microscope optics according to some embodiments of the present invention.

FIG. 16 illustrates embodiments of the present invention for incorporation of an OCT sample arm unit 1500 into an intrasurgical microscope 1100 for obtaining OCT images of the ocular anterior segment with the improved resolution and brightness supported by the physical dimensions of the microscope 1100, while maintaining compatibility for matching the field of view of the OCT and microscope views and reducing or avoiding OCT image vignetting. The OCT sample arm beam is introduced into the optical path of the microscope 1100 in the infinity space above the shared main objective 1102 of the microscope 1100 (and prior to the illumination unit 1110, the microscope optics 1104 (including channels 1112, 1114) and the eye pieces 1106), by use of a dichroic beamsplitter 1400 which reflects OCT wavelengths (typically in the near infrared) while transmitting visible wavelengths carrying the white light microscope image to the optical imaging channels 1112, 1114 above. Such a dichroic mirror is typically referred to as a "hot mirror." The OCT sample arm beam is assumed to be delivered to the vicinity of the microscope 1110 in the form of a collimated narrow beam (with beam width typically 2-4 mm) at the left of FIG. 16. Such a collimated narrow beam may result from sample arm light exiting a single mode optical fiber and impinging upon a collimating lens 1502 with focal length $f_7$, as shown in FIG. 16, or it may impinge directly from a bulk-optic OCT system lacking optical fibers. The narrow OCT sample arm beam is incident on a pair of orthogonal optical scanners 1504, depicted as a bolded cross in FIG. 16. Many different scanning technologies can and have been used in OCT systems, although the most typical are limited-angle galvanometer scanners. Most scanning technologies however share the attributes that their cost and performance is typically inversely proportional to the size of their optical aperture; this is why they are typically employed in OCT systems where the sample arm beam is narrow. In FIG. 16, an orthogonally oriented pair of scanners 1504 is indicated, capable of scanning the narrow OCT sample arm beam over a limited range of angles in two dimensions under computer control. It will be obvious to one skilled in the art of optical scanning systems that such a pair may be constructed from a single mirror having the capability of pivoting in two dimensions, or a pair of single-axis galvanometer scanners located in close proximity (which is the most common arrangement), or a pair of single-axis galvanometer scanners with the optical aperture of one being imaged into the optical aperture of the other using, for example, a standard 4f optical imaging system comprised of a pair of lenses. It is to be understood that any of these technologies may be used and equivalently represented by the cross symbol depicted in FIG. 16.

A beam-forming optical assembly including lenses 1508 and 1510 is positioned between the 2D scanners and the OCT beamsplitter above the shared main objective 1102 of the microscope. The design purpose of the optical assembly is to match the size, divergence, and scanning geometry of the OCT sample arm beam to the maximum capabilities supported by the microscope. In FIG. 16, this is accomplished using an adjustable Keplerian telescope as a beam expander which is placed at the proper position with respect to the microscope 1100, although other possible optical designs could be used to accomplish the same objective (such as, most simply, a Galilean teslescope). For the beam forming optical assembly depicted in FIG. 16, the optical design parameters are as follows. The ratio of the focal lengths of the two lenses $f_5$ and $f_6$ may be chosen so that the narrow OCT beam with $1/e^2$ beam diameter $a_6$ is expanded to approximately fill the back aperture of the shared main microscope objective $a_3$. This is accomplished when:

$$\frac{f_5}{f_6} = \frac{a_3}{a_6}. \qquad \text{Eq. (7)}$$

In order that the divergence of the OCT sample beam generally match the divergence of the microscope image light above the shared objective 1102 which may not be exactly parallel, and therefore provide the capability to closely match the position within the patient's eye of the OCT focus to that of the microscope, some variability should be provided in the position of either or both of lenses 1510 ($f_5$) or 1508 $f_6$, as depicted in FIG. 16. This can be accomplished by mounting one or both lenses on a mechanical stage which can be adjusted manually or electronically by the surgeon or an assistant while viewing both images. For this purpose, an adjustment range of either lens of approximately 5% of its focal length will suffice.

In order to reduce or prevent vignetting of the OCT beam during scanning, while simultaneously making use of the entire optical aperture of the shared objective at the same time, optimal design of the beam-forming optical assembly includes provision that the OCT beam pivot through the main objective rather than scan across it. In general, this may be accomplished by designing the optical assembly in such a way as to optically image the optical scanner plane into the back aperture of the main objective 1102. For the Keplerian telescope shown in FIG. 16, this can be accomplished by placement of the lenses of the telescope relative to the scanner and objective location, such that the following relationship among the distances between the lenses is satisfied:

$$d_6=f_6;\ d_5=f_5+f_6;\ d_4=f_5 \qquad \text{Eq. (8)}$$

Here, it is to be understood that the distances $d_4$, $d_5$, etc. correspond to the center-to-center distances between the lenses referred to. Also, it is to be understood that the relationships given in all of these design equations are simplified according to the assumption that all of the lenses act as ideal lenses which is appropriate for first-order design. For production design, professional lens design software should be used to optimize higher order performance, however following the principles described herein. The beamforming optical assembly may be employed, for example, in the configurations illustrated in FIGS. 2A-2B, 3 and 4.

In the configuration illustrated in FIG. 16, generally all of the OCT optical elements which are positioned either within the microscope body itself, or else sufficiently high up on the microscope body that the OCT assembly may not interfere with the surgeon's view of or access to the patient. However, this configuration may lengthens the overall height of the surgical microscope by displacing the optical imaging channels upward in order to make room for the beamsplitter, which may be inconvenient for the surgeon. Secondly, the main objective is dually-utilized for OCT in addition to white light imaging, which it may not be well designed for.

Figure 17:
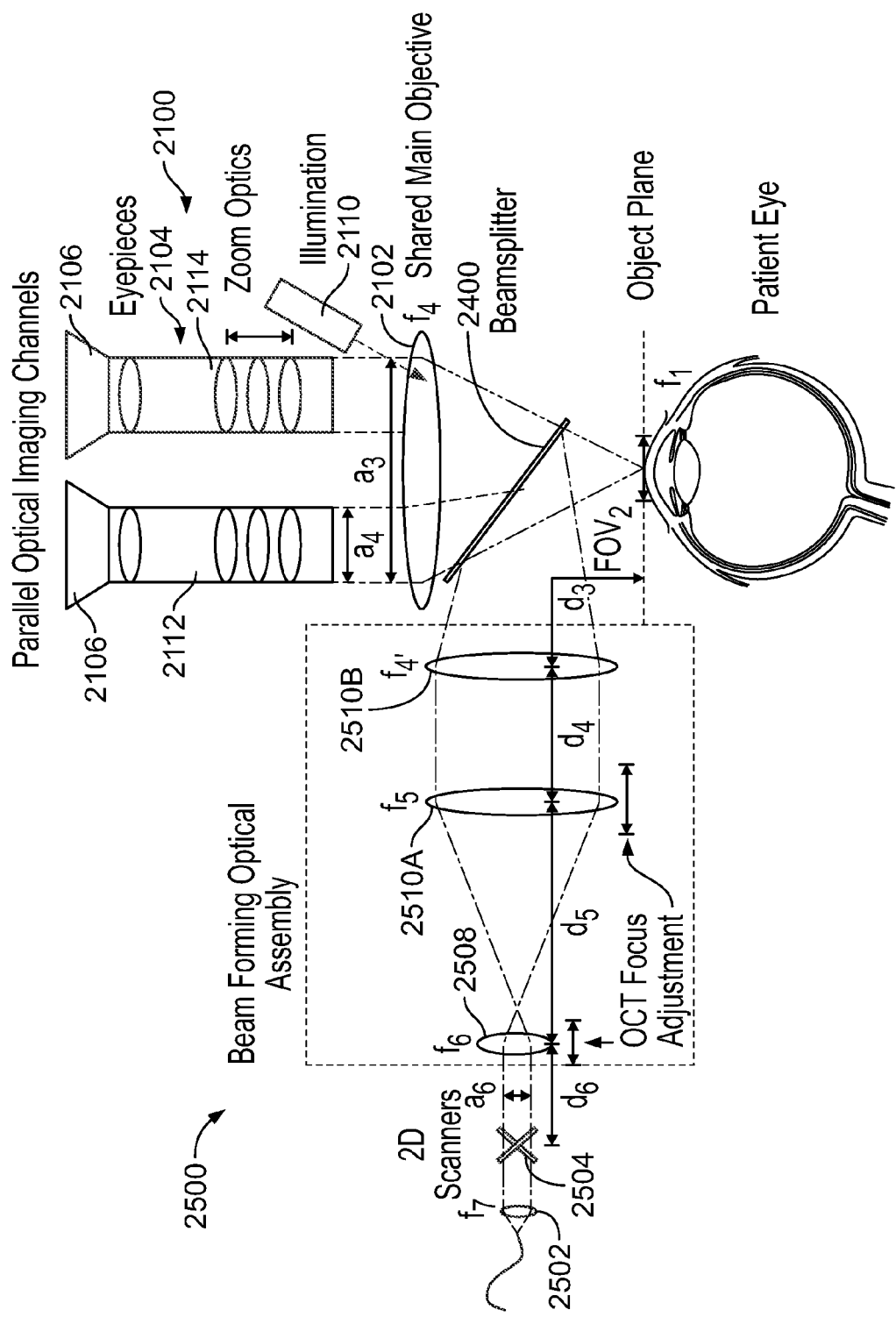
FIG. 17 is a schematic diagram illustrating an OCT scanner and beam forming assembly coupled to the microscope according to some embodiments of the present invention.

FIG. 17 illustrates an OCT unit 2500 and a microscope 2100. The OCT unit includes a collimating lens 2502, scanners 2504 and a beam forming optical assembly having a optics or lenses 2508, 2510A and 2510B, which are impinged on a beamsplitter 2400. The microscope 2100 includes a shared main objective 2102, an illumination unit 2110, microscope optics 2104 having dual channels 2112, 2114 and respective eyepieces 2106. In this configuration, OCT may be incorporated into an intrasurgical microscope for obtaining OCT images of the anterior segment with the improved resolution and brightness supported by the physical dimensions of the microscope 2100, while maintaining compatibility for matching the field of view of the OCT and microscope views and avoiding OCT image vignetting. Unlike the configuration of FIG. 16, the OCT sample arm beam is introduced using a beamsplitter 2400 below the shared main objective of the microscope, thus avoiding use of that objective for the OCT beam. To compensate optically for not using the main objective 2102, an additional lens 2510B with focal length $f_4$, Is introduced into the beam forming optical assembly. With the design in FIG. 17, if a lens 2510B for $f_a$, is chosen with the same focal length as the main shared objective 2102 of the microscope $f_a$, then Eqs. (7) and (8) still apply, and the beamsplitter and beam-forming optical assembly should be positioned such that:

$$d_a=f_4^- \qquad \text{Eq. (9)}$$

However, the design depicted in FIG. 17 gives some additional optical design flexibility such that lens $f_a$, need not be chosen to exactly match the focal length of the shared main objective $f_4$, so long as the additional optics in the beam forming assembly are chosen to match the OCT beam size and divergence to the NA of the shared main objective at the position of the beamsplitter 2400.

Figure 18:
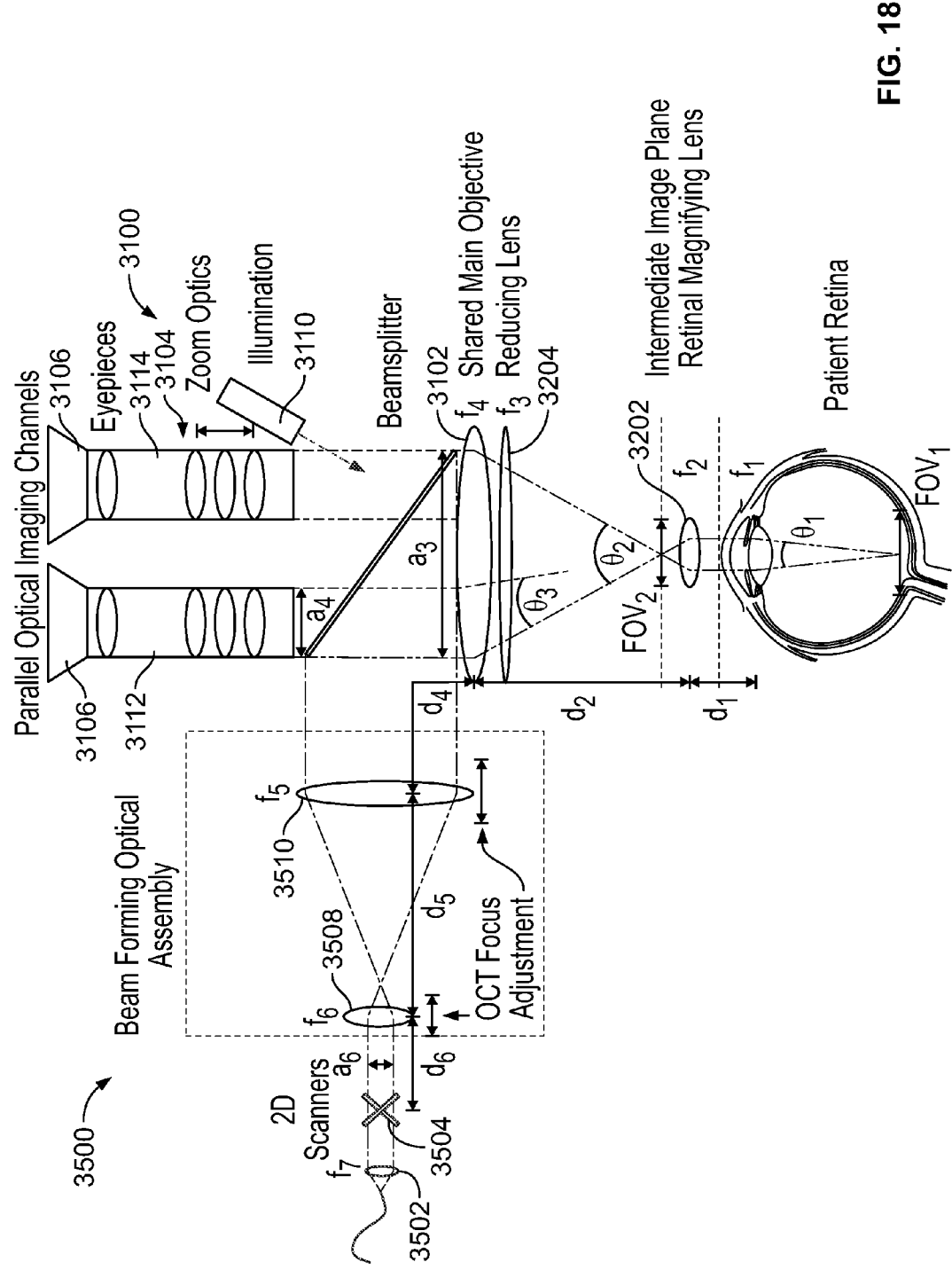
FIG. 18 is a schematic diagram illustrating an OCT scanner and beam forming assembly coupled to the microscope optics configured to view an ocular fundus region according to some embodiments of the present invention.

FIG. 18 illustrates an OCT unit 3500 and a microscope 3100 having a vitreoretinal viewing unit 3200. The OCT unit includes a collimating lens 3502, scanners 3504 and a beam forming optical assembly having a optics or lenses 3508, 3510, which are impinged on a beamsplitter 3400. The microscope 3100 includes a shared main objective 3102, an illumination unit 3110, microscope optics 3104 having dual channels 3112, 3114 and respective eyepieces 3106. The vitreoretinal viewing unit 3200 includes a contact lens 3202 and a reduction lens 3204. In this configuration, OCT may be incorporated into an intrasurgical microscope 3100 for obtaining OCT images of the retina and macula with increased resolution and brightness supported by the physical dimensions of the microscope 3100, while maintaining compatibility for matching the field of view of the OCT 3500 and microscope views and avoiding OCT image vignetting. In this invention, the OCT sample arm beam is introduced into the optical path of the microscope 3100 in the infinity space above the shared main objective 3102 of the microscope, by use of a dichroic beamsplitter 3400 which reflects OCT wavelengths (typically in the near infrared) while transmitting visible wavelengths carrying the white light microscope image to the optical imaging channels above. Such a dichroic mirror is typically referred to as a "hot mirror." The OCT sample arm beam is assumed to be delivered to the vicinity of the microscope 3100 in the form of a collimated narrow beam (with beam width typically 2-4 mm) at the left of FIG. 18. Such a collimated narrow beam may result from sample arm light exiting a single mode optical fiber and impinging upon a collimating lens 3502 with focal length $f_7$, as depicted in FIG. 18, or it may impinge directly from a bulk-optic OCT system lacking optical fibers. The narrow OCT sample arm beam is incident on a pair of orthogonal optical scanners 3504, depicted as a bolded cross in FIG. 18. Many different scanning technologies can and have been used in OCT systems, although the most typical are limited-angle galvanometer scanners. Most scanning technologies however share the attributes that their cost and performance is typically inversely proportional to the size of their optical aperture; this is why they are typically employed in OCT systems where the sample arm beam is narrow. In FIG. 18 an orthogonally oriented pair of scanners is indicated, capable of scanning the narrow OCT sample arm beam over a limited range of angles in two dimensions under computer control. It will be obvious to one skilled in the art of optical scanning systems that such a pair may be constructed from a single mirror having the capability of pivoting in two dimensions, or a pair of single-axis galvanometer scanners located in close proximity (which is the most common arrangement), or a pair of single-axis galvanometer scanners with the optical aperture of one being imaged into the optical aperture of the other using, for example, a standard 4f optical imaging system comprised of a pair of lenses. It is to be understood that any of these technologies may be used and equivalently represented by the cross symbol depicted in FIG. 18.

As illustrated, the beam-forming optical assembly is positioned between the 2D scanners 3504 and the OCT beamsplitter 3400 above the shared main objective 3102 of the microscope 3100. The design purpose of the optical assembly is to match the size, divergence, and scanning geometry of the OCT sample arm beam to the maximum capabilities supported by the microscope 3100. In FIG. 18, this is accomplished using a simple, adjustable Keplerian telescope as a beam expander which is placed at the proper position with respect to the microscope, although other possible optical designs could be used to accomplish the same objective (such as, most simply, a Galilean teslescope). For the beam former depicted in FIG. 18, the optical design parameters are as follows. The ratio of the focal lengths of the two lenses 3510 ($f_5$) and 3508 ($f_6$) may be chosen so that the narrow OCT beam with $1/e^2$ beam diameter $a_6$ is expanded to approximately fill the back aperture of the shared main microscope objective $a_3$. This is accomplished when:

$$\frac{f_5}{f_6} = \frac{a_3}{a_6}. \qquad \text{Eq. (10)}$$

In order that the divergence of the OCT sample beam generally match the divergence of the microscope image light above the shared objective which may not be exactly parallel, and therefore provide the capability to closely match the position within the patient's retina of the OCT focus to that of the microscope, some variability should be provided in the position of either or both of lenses 3510 ($f_5$) and 3508 ($f_6$), as depicted in FIG. 18. This can be accomplished by mounting one or both lenses on a mechanical stage which can be adjusted manually or electronically by the surgeon or an assistant while viewing both images. For this purpose, an adjustment range of either lens of approximately 5% of its focal length will suffice.

In order to reduce or prevent vignetting of the OCT beam during scanning, while simultaneously making use of the entire optical aperture of the shared objective at the same time, optimal design of the beam-forming optical assembly includes provision that the OCT beam pivot through the main objective rather than scan across it. In general, this can be accomplished by designing the optical assembly in such a way as to optically image the optical scanner plane into the main objective back aperture. For the Keplerian telescope depicted in FIG. 18, this is accomplished by placement of the lenses of the telescope relative to the scanner and objective location, such that the following relationship among the distances between the lenses is satisfied:

$$d_6 = f_6; \ d_5 = f_5 + f_6; \ d_4 = f_5 \qquad \text{Eq. (11)}$$

Furthermore, for OCT imaging of a patient's retina with increased or maximum resolution and image brightness, the OCT sample arm beam may be designed at the position of the patient's cornea to have a beam diameter which is the maximum over which a human's eye is approximately diffraction limited (typically 2-3 mm), and that the scanning OCT beam pivot through the patient's iris plane rather than scan across it, so that the entire available optical aperture is used for all scan widths without vignetting. The first condition on beam size at the cornea is satisfied by realizing that the lenses 3203 ($f_2$), 3204 ($f_3$), and 3102 ($f_4$) operate essentially as a Keplerian beam reducer. As a simplifying assumption, the reducing lens 3204 ($f_3$) typically has much less optical power than the main objective 3102 ($f_4$), and is located directly adjacent to it. Then, these two lenses can be considered as operating together as a single lens, with optical power given by the sum of the optical powers of the lenses individually, and located at the position of the main objective 3102. According to this approximation, the main objective 3102 is replaced by a modified main objective with focal length $f_4$, according to:

$$\frac{1}{f_4'} = \frac{1}{f_3} + \frac{1}{f_4} \qquad \text{Eq. (12)}$$

Now the design condition on the choice of lenses f2 and f4' to ensure the correct beam size on the patient's cornea is given by:

$$\frac{f_4'}{f_2} = \frac{a_3}{a_1}, \qquad \text{Eq. (13)}$$

where a1 is the desired collimated beam size on the cornea. Finally, in order to have the OCT beam pivot through the patients' iris plane rather than scan across it, the position of lens $f_2$ should be set so that it forms a real image of the aperture of the shared main objective at the location of the patient's iris plane. Thus the distances $d_1$ and $d_2$ (which equals $f_4'+f_2$) should be set according to:

$$\frac{1}{f_2} = \frac{1}{f_2 + f_4'} + \frac{1}{d_1} \qquad \text{Eq. (14)}$$

As a practical design procedure, $f_2$ and $f_3$ should be chosen according to Eq. (12) and (13) given the constraint the microscope imposes on $f_4$, then $d_1$ may be chosen according to Eq. (14). The beamforming optical assembly may be employed, for example, in the configurations illustrated in FIGS. 2A-2B, 3 and 4.

In the foregoing, it is to be understood that the distances $d_4$, $d_5$, etc. correspond to the center-to-center distances between the lenses referred to. Also, it is to be understood that the relationships given in all of these design equations are simplified according to the assumption that all of the lenses act as ideal lenses which is appropriate for first-order design. For production design, professional lens design software may be used to optimize higher order performance, however following the principles described here.

In the configuration illustrated in FIG. 18, all of the OCT optical elements are generally positioned either within the microscope body itself, or else sufficiently high up on the microscope body that the OCT assembly will not interfere with the surgeon's view of or access to the patient. However, this configuration may lengthen the overall height of the surgical microscope by displacing the optical imaging channels upward in order to make room for the beamsplitter, which may be inconvenient for the surgeon. Secondly, the configuration illustrated in FIG. 18 dual-utilizes the main objective for OCT in addition to white light imaging, which it may not be well designed for.

Figure 19:
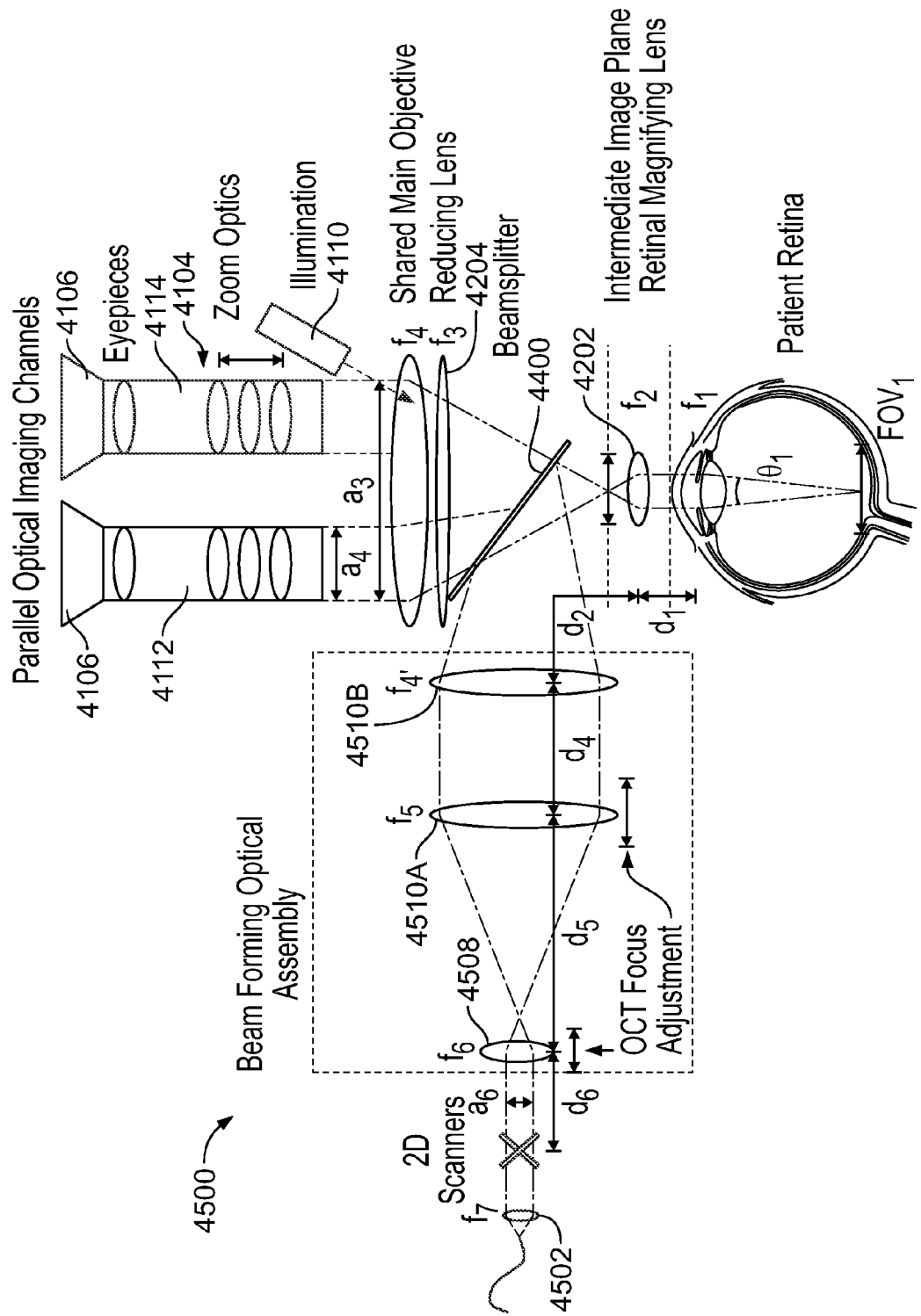
FIG. 19 is a schematic diagram illustrating an OCT scanner and beam forming assembly coupled to the microscope configured to view an ocular fundus region according to some embodiments of the present invention.

FIG. 19 illustrates an OCT unit 4500 and a microscope 4100 having a vitreoretinal viewing unit 4200. The OCT unit includes a collimating lens 4502, scanners 4504 and a beam forming optical assembly having a optics or lenses 4508, 4510A, and 4510B, which are impinged on a beamsplitter 4400. The microscope 4100 includes a shared main objective 4102, an illumination unit 4110, microscope optics 4104 having dual channels 4112, 4114 and respective eyepieces 4106. The vitreoretinal viewing unit 4200 includes a contact lens 4202 and a reduction lens 4204. In this configuration, OCT may be incorporated into an intrasurgical microscope 4100 for obtaining OCT images of the macula and retina with increased resolution and brightness supported by the physical dimensions of the microscope 4100, while maintaining compatibility for matching the field of view of the OCT and microscope views and avoiding OCT image vignetting. Unlike the configuration of FIG. 18, in the configuration illustrated in FIG. 19, the OCT sample arm beam is introduced using a beamsplitter 4400 below the shared main objective 4102 of the microscope, thus avoiding use of that objective for the OCT beam. To compensate optically for not using the main objective 4102, an additional lens 4510B with focal length $f_{4'}$. Is introduced into the beam forming optical assembly. As illustrated, if a lens 4510B for $f_{4'}$ is chosen with the same focal length as the combination of the main shared objective 4102 of the microscope $f_4$ and the reducing lens $f_3$, then Eqs. (10)-(14) still apply, and the beamsplitter and beamforming optical assembly should be positioned such that:

$$d_2 = f_4' + f_2.\qquad\text{Eq. (15)}$$

However, in the configuration of FIG. 19, some additional optical design flexibility may be achieved, such that lens 4410B ($f_4$) may not be chosen to exactly match the focal length of the shared main objective 4102 ($f_4$) and the reducing lens 4204 ($f_3$), so long as the additional optics in the beam forming assembly are chosen to match the OCT beam size and divergence to the NA of the shared main objective 4102 and reducing lens 4204 at the position of the beamsplitter 4400.

In some embodiments, improvements in surgical visualization may impact the treatment of a wide range of ocular diseases including diabetic retinopathy with membranes in the macula, macular holes, epiretinal membranes, and retinal detachments. Real-time cross-sectional OCT imaging may also provide information relevant to the location and deformation of structures that may shift during surgery.

Although embodiments according to the present invention are described herein with respect to ocular imaging, it should be understood that any sample may be used, including in vivo or ex vivo biological samples. For example, embodiments according to the present invention may be usefule for surgical margin assessment during cancer surgery.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A surgical microscope assembly including microscope imaging optics having a microscope main objective, the microscope imaging optics defining one or more viewing beam paths that pass from a sample through the microscope main objective and the microscope imaging optics, the assembly comprising:
    an optical coherence tomography (OCT) unit having an illumination beam and a collection beam;
    a beamsplitter positioned in the one or more microscope viewing beam paths, the beamsplitter being configured to direct a portion of light from the sample to the microscope imaging optics and to direct another portion of light from the sample to the OCT unit collection beam, the beamsplitter being further configured to direct an illumination beam from the OCT unit to the sample; and
    a beam forming unit between the OCT unit and the beamsplitter, the beam forming unit configured to form the illumination beam of the OCT unit so as to correspond to a size of the microscope main objective.

2. The surgical microscope assembly of claim 1 further comprising a vitreoretinal viewing optics unit configured to transmit light received from the sample to the microscope main objective for vitreoretinal imaging by the microscope imaging optics and to receive the illumination beam of the OCT unit from the microscope main objective.

3. The surgical microscope assembly of claim 2 wherein the vitreoretinal viewing optics unit comprises a contact lens element for contacting a sample.

4. The surgical microscope assembly of claim 2 wherein the vitreoretinal viewing optics unit comprises a non-contact lens configured for positioning adjacent the sample and a reduction lens configured for positioning adjacent the microscope main objective.

5. The surgical microscope assembly of claim 1 wherein the beam splitter comprises a dichroic mirror.

6. The surgical microscope assembly of claim 1 wherein the beam forming unit is configured to form the illumination beam of the OCT unit so as to correspond to a size of a binocular viewing path area of the microscope main objective.

7. The surgical microscope assembly of claim 1, wherein the beam forming unit is configured to magnify the illumination beam of the OCT unit.

8. The surgical microscope assembly of claim 1, wherein the sample comprises an ocular sample.

9. The surgical microscope assembly of claim 1, wherein the sample comprises an ocular fundus.

10. The surgical microscope assembly of claim 1, wherein the beam forming optical assembly comprises an adjustable Keplerian telescope.

11. The surgical microscope assembly of claim 1, wherein the beam forming optical assembly comprises at least two lenses being configured to adjustably focus and/or magnify the illumination beam of the OCT unit.

12. The surgical microscope assembly of claim 1, wherein the microscope imaging optics include microscope magnification optics, and the beamsplitter is positioned between the microscope main objective and the microscope magnification optics.

13. The surgical microscope assembly of claim 1, wherein the beam forming unit is configured to form the illumination beam of the OCT unit so as to reduce image vignetting.

14. A surgical microscope assembly including microscope imaging optics having a microscope main objective, the microscope imaging optics defining a viewing beam path that passes from a sample through the microscope main objective and the microscope imaging optics, the assembly comprising:
    an optical coherence tomography (OCT) unit having an illumination beam and a collection beam;
    a beamsplitter configured to direct a portion of light from the sample to the to the microscope main objective and to direct another portion of light from the sample to the OCT unit, the beamsplitter being further configured to direct light from the illumination beam of the OCT unit to the sample; and
    a beam forming unit between the OCT unit and the beamsplitter and configured to form the illumination beam of the OCT unit to substantially correspond to a beam path of the microscope main objective.

15. The surgical microscope assembly of claim 14, further comprising a vitreoretinal viewing optics unit configured to transmit light received from the sample to the microscope main objective for vitreoretinal imaging by the microscope imaging optics.

16. The surgical microscope assembly of claim 14, the vitreoretinal viewing optics unit comprising a non-contact lens configured for positioning adjacent the sample and a reduction lens configured for positioning adjacent the microscope main objective, and the non-contact lens and the reduction lens are configured to provide a vitreoretinal view of an ocular sample.

17. The surgical microscope assembly of claim 14, wherein the beamsplitter is positioned between the non-contact lens and the reduction lens.

18. The surgical microscope assembly of claim 14, wherein the beam splitter comprises a dichroic mirror.

19. The surgical microscope assembly of claim 14, wherein the beam forming unit is configured to form the illumination beam of the OCT unit so as to correspond to a size of a binocular viewing path area of the microscope main objective.

20. The surgical microscope assembly of claim 14, wherein the sample comprises an ocular sample.

21. The surgical microscope assembly of claim 14, wherein the sample comprises an ocular fundus.

22. The surgical microscope assembly of claim 14, wherein the beam forming optical assembly comprises an adjustable Keplerian telescope.

23. The surgical microscope assembly of claim 14, wherein the beam forming optical assembly comprises at least two lenses being configured to adjustably focus and/or magnify the illumination beam of the OCT unit.

24. A method of imaging a sample with an optical coherence tomography (OCT) unit having an illumination beam and a collection beam and a microscope having microscope imaging optics with a microscope main objective, the method comprising:
- directing a portion of light from the microscope main objective to additional portions of the microscope imaging optics;
- directing another portion of light from the microscope main objective to the OCT unit collection beam;
- forming the illumination beam of the OCT unit to correspond to a beam path of the microscope main objective; and
- directing the formed illumination beam from the OCT unit to the microscope main objective and to the sample.

25. A method of imaging a sample with an optical coherence tomography (OCT) unit having an illumination beam and a collection beam and a microscope having a main objective and microscope imaging optics, the method comprising:
- directing a portion of light from the sample to the to the microscope main objective;
- directing another portion of light from the sample to the OCT unit collection beam;
- forming the illumination beam of the OCT unit to correspond to a beam path of the microscope main objective; and
- directing formed light from the illumination beam of the OCT unit to the sample.

* * * * *